US009575010B2

(12) United States Patent
Ogawa et al.

(10) Patent No.: US 9,575,010 B2
(45) Date of Patent: Feb. 21, 2017

(54) INSPECTION APPARATUS AND INSPECTION METHOD

(71) Applicant: NuFlare Technology, Inc., Yokohama (JP)

(72) Inventors: Riki Ogawa, Kanagawa (JP); Nobutaka Kikuiri, Tokyo (JP); Hideaki Hashimoto, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 15/180,222

(22) Filed: Jun. 13, 2016

(65) Prior Publication Data

US 2016/0370300 A1    Dec. 22, 2016

(30) Foreign Application Priority Data

Jun. 19, 2015   (JP) ................................. 2015-123936

(51) Int. Cl.
*G01N 21/88* (2006.01)
*G01N 21/956* (2006.01)

(52) U.S. Cl.
CPC ...... *G01N 21/8851* (2013.01); *G01N 21/8806* (2013.01); *G01N 21/956* (2013.01); *G01N 2021/8848* (2013.01); *G01N 2021/8887* (2013.01)

(58) Field of Classification Search
CPC .............................. G06T 7/001; G06T 7/0008
USPC ..................................................... 356/237.5
See application file for complete search history.

(56) References Cited

U.S. PATENT DOCUMENTS

| 9,196,033 | B2* | 11/2015 | Hashimoto | ............. G06T 7/001 |
| 2011/0096324 | A1* | 4/2011 | Watanabe | ............ G01N 21/956 |
| | | | | 356/237.5 |
| 2014/0072202 | A1* | 3/2014 | Ogawa | ................. G01N 21/956 |
| | | | | 382/145 |
| 2014/0310662 | A1 | 10/2014 | Hashimoto | |
| 2016/0267648 | A1* | 9/2016 | Yamashita | ............ G06T 7/0008 |

FOREIGN PATENT DOCUMENTS

| JP | 2012-220388 | 11/2012 |
| JP | 2014-206446 | 10/2014 |

* cited by examiner

*Primary Examiner* — Roy M Punnoose
(74) *Attorney, Agent, or Firm* — Oblon, McClelland, Maier & Neustadt, L.L.P.

(57) ABSTRACT

An inspection object is supported by a table. Light is emitted from a light source to illuminate the inspection object. An optical unit illuminates the inspection object with light, wherein the light is transmitted through the inspection object. Another optical unit illuminates the inspection object with light, wherein the light is reflected by the inspection object. Light transmitted through the inspection object is incident to a first sensor. Light reflected by the inspection object is incident to a second sensor. A defect of a pattern of the inspection object is detected using optical image data output from at least one of the sensors. A line width error is obtained by comparing line widths obtained from design data and optical image data of the pattern. A polarized beam splitter is disposed, movable between the inspection object and the first sensor, and between the inspection object and the second sensor.

20 Claims, 13 Drawing Sheets

INSPECTION APPARATUS AND INSPECTION METHOD

CROSS-REFERENCE TO THE RELATED APPLICATION

The entire disclosure of the Japanese Patent Application No. 2015-123936, filed on Jun. 19, 2015 including specification, claims, drawings, and summary, on which the Convention priority of the present application is based, are incorporated herein in its entirety.

FIELD OF THE INVENTION

The present invention relates to an Inspection Apparatus and an Inspection Method.

BACKGROUND

In a production process of a semiconductor element, an original pattern in which a circuit pattern is formed, that is, a mask or a reticle (hereinafter collectively referred to as a mask) is exposed and transferred onto a wafer by a reduction projection exposure apparatus called a stepper or a scanner. Since production of a Large Scale Integration (LSI) requires a large manufacturing cost, it is crucial to improve the production yield. A defect of a mask pattern can be cited as a large factor of degradation in the production yield of a semiconductor element.

Further, in the inspection process, not only is the detection of a defect performed, but also, measurement of a line width (CD) of a pattern formed in a mask is performed, to generate a map of a distribution of a difference value (line width error: ΔCD) between the measured value of the line width and the design value of the pattern. The obtained ΔCD map is then fedback to the mask production process to be used for revising the condition of the process.

Document 1 (Japanese Unexamined Patent Application Publication No: 2012-220388) discloses an inspection apparatus for inspecting a mask by dividing light emitted from a light source to two light paths, wherein one light path illuminates a mask to be inspected by light transmitted through the mask, and another path illuminates the mask by light reflected by the mask, thereby obtaining an optical image of the pattern of the mask by a sensor in which the light transmitted through the mask is incident, and another sensor in which the light reflected by the mask is incident. In this inspection apparatus, a polarized beam splitter is disposed along the light path from the mask to the sensor. Further, this polarized beam splitter is also disposed along the light path for illuminating the mask with the light to be reflected. That is, the light reflected by the polarized beam splitter illuminates, and is then reflected by, the mask, and is incident to the sensor after returning through the polarized beam splitter.

Generally, a mask consists of a quartz glass substrate, and a pattern consisting of a light shielding film comprising a chrome film formed on the surface of quartz glass substrate. The quartz glass substrate has birefringence, and the direction of the birefringence is different depending on the position of the inside of the substrate as a result of distortion, etc. Therefore, the polarized state of the light before transmission through the mask is then changed to a different polarized state after the light is transmitted through the mask, as a result there is a problem in that the light quantity of the light transmitted through the polarized beam splitter is decreased. Specifically, the light before transmission through the mask is circularly polarized light, whereas on the other hand, the light after transmission through the mask is elliptical-polarized light, depending on the difference of the direction of the birefringence in the mask. The light transmitted through the mask is changed by a quarter-wavelength plate from the circularly polarized light to the linearly polarized light having only a p-polarized component for the polarized beam splitter, thereby allowing transmission through the polarized beam splitter. However, because the elliptical polarized light is incident to the quarter-wavelength plate, the light to be incident to the polarized beam splitter is: non-linearly polarized light, or a linearly polarized light having the s-polarized component. As a result the light quantity of the light to be transmitted through the polarized beam splitter is decreased.

In order to resolve the above-mentioned problem, in Document 1, the quartz glass substrate in which a pattern is not formed, is illuminated before the inspection for detecting a defect, and then the transmitted light is incident to the sensor in order to generate brightness distribution data. Then, a brightness value of an actual inspection is corrected using the brightness distribution data. However, it takes a great deal of time to obtain the brightness distribution data for every before the inspection. Document 1 also does not disclose a generation of a ΔCD map.

An object of the present invention is to provide an inspection apparatus and an inspection method that can perform inspection to detect a defect easily and accurately by decreasing an effect by birefringence of a quartz glass substrate, and can obtain an accurate line width error in order to generate an accurate ΔCD map. Other advantages and challenges of the present invention are apparent from the following description.

SUMMARY OF THE INVENTION

According to one aspect of the present invention, an inspection apparatus for inspecting an inspection object to detect the existence of a defect using optical image data obtained by illuminating light to transmit through, and reflect from the inspection object, to be incident to respective sensors, and to compare the obtained optical image data with design data to determine the existence of a defect. The inspection apparatus includes a table, a position measuring unit, a light source, an illuminating optical unit including a transmissive illuminating optical unit and a reflective illuminating optical unit, a first sensor, a second sensor, a comparing unit, a line width error obtaining unit, and a polarized beam splitter. The table supports the inspection object. The position measuring unit measures a position coordinate of the table. The light source emits light for illuminating the inspection object. The transmissive illuminating optical unit illuminates the inspection object with light emitted from the light source, the light is then transmitted through the inspection object. The reflective illuminating optical unit illuminates the inspection object with light emitted from the light source, the light is then reflected by the inspection object. The first sensor for converting an optical image of the inspection object to an electric signal, whereon the light transmitted through the inspection object by the transmissive illuminating optical unit is incident. The second sensor for converting an optical image of the inspection object to an electric signal, whereon the light reflected by the inspection object by the reflective illuminating optical unit is incident. The comparing unit to detect a defect of a pattern of the inspection object by comparing optical image data output from at least one of the first sensor and the second sensor with reference image data generated from design data of the pattern, corresponding to the optical image data. The line width error obtaining unit to obtain a line width error by comparing a line width from design data of the pattern and a line width of the pattern from the optical image data. The polarized beam splitter is movable between the inspection object and the first sensor, and between the inspection object and the second sensor, and in the case where the polarized beam splitter is disposed along the light path of the light for illuminating the inspection object with the light to be transmitted, the polarized beam splitter is also disposed along the light path for illuminating the inspection object with the light to be reflected.

According to another aspect of the present invention, an inspection method includes obtaining optical image data by illuminating an inspection object, transmitting the light through the inspection object and a polarized beam splitter, and causing the light transmitted through the polarized beam splitter to be incident to a first sensor to convert an optical image of the inspection object to an electric signal, and further, by illuminating the inspection object, transmitting the light reflected by the inspection object through the polarized beam splitter, and causing the light transmitted through the polarized beam splitter to be incident to a second sensor to convert an optical image of the inspection object to an electric signal. The obtained optical image data is used to detect a defect of a pattern of the inspection object. Other optical image data is obtained by illuminating the inspection object, transmitting the light through the inspection object be incident to a first sensor, without transmission through the polarized beam splitter, to convert an optical image of the inspection object to an electric signal. A difference is obtained between a line width obtained from design data of the pattern, and a line width obtained from the pattern of the optical image data obtained without transmission through the polarized beam splitter.

According to another aspect of the present invention, an inspection method includes obtaining optical image data by illuminating an inspection object, transmitting the light through the inspection object and a polarized beam splitter, and causing the light transmitted through the polarized beam splitter to be incident to a first sensor to convert an optical image of the inspection object to an electric signal, and further, by illuminating the inspection object, transmitting the light reflected by the inspection object through the polarized beam splitter, and causing the light transmitted through the polarized beam splitter to be incident to a second sensor to convert an optical image of the inspection object to an electric signal. The obtained optical image data is used to detect a defect of a pattern of the inspection object. A difference is obtained between a line width obtained from design data of the pattern, and a line width of the pattern of the optical image data. Optical image data is obtained of a predetermined area of the inspection object by illuminating the inspection object by light emitted from a light source, causing the light transmitted through the inspection object to be incident to the first sensor without transmission through the polarized beam splitter, and converting the optical image of the inspection object to an electric signal by the first sensor. A correction is performed using the obtained line widths.

BRIEF DESCRIPTION OF THE DRAWINGS

A more complete appreciation of the present invention and many of the advantages thereof will be readily obtained as the present invention becomes better understood by reference to the following detailed description when considered in connection with the accompanying drawings, wherein.

DETAILED DESCRIPTION OF THE EMBODIMENT

Figure 1:
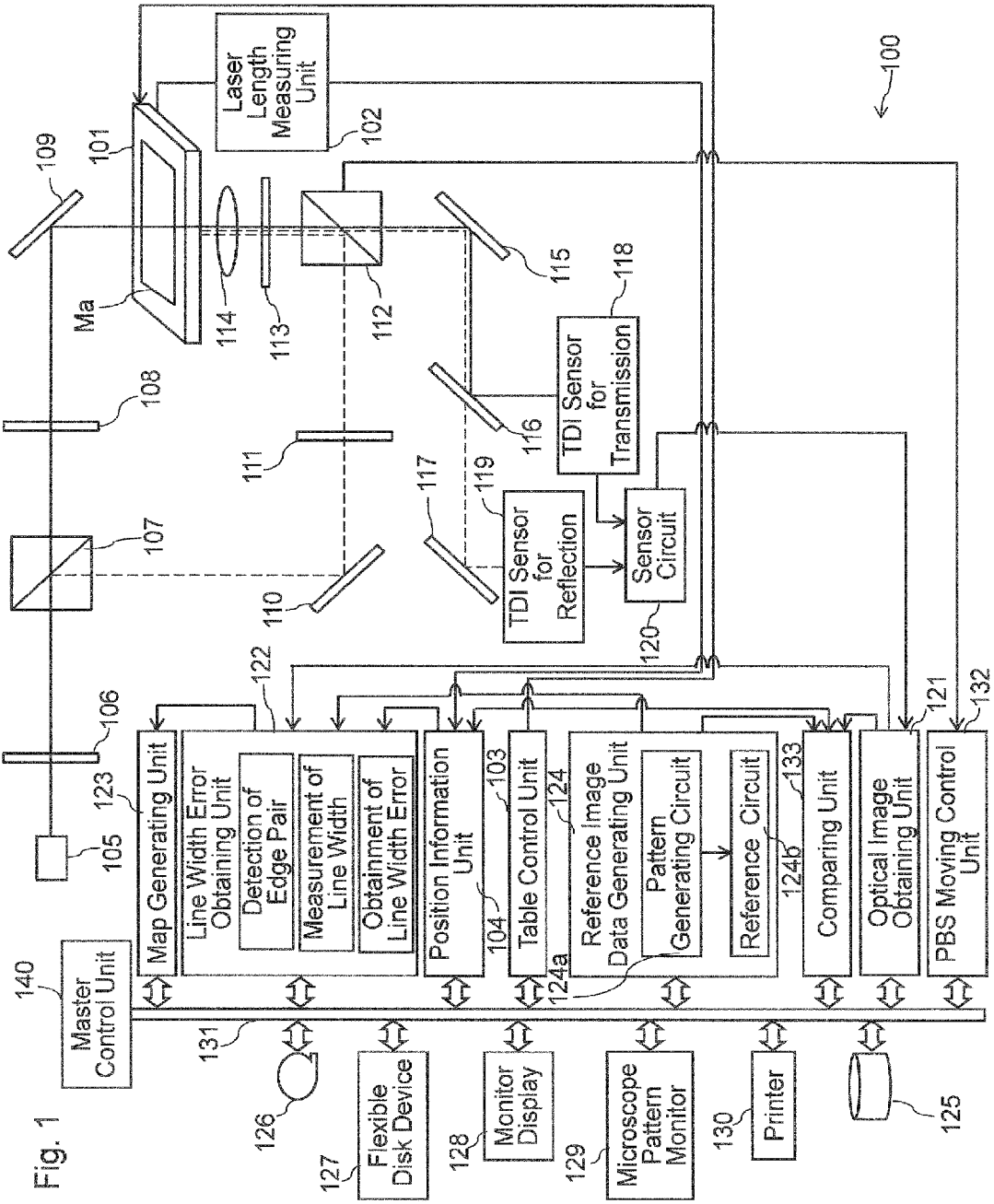
FIG. 1 is a schematic configuration diagram of the inspection apparatus according to the first embodiment.

The embodiments will now be described with reference to the accompanying drawings, wherein the same reference numerals designate corresponding or identical elements throughout the various drawings.

First Embodiment

FIG. 1 is a schematic configuration diagram of the inspection apparatus 100 according to the present embodiment. The inspection apparatus 100 detects a defect in the inspection object by obtaining optical image data of the inspection object, and then compares the optical image data corresponding to reference image data. Further, the inspection apparatus 100 obtains a line width error ($\Delta$CD) of the inspection object, and then generates a line width error map ($\Delta$CD map) from the line width error. The fundamental construction of the inspection apparatus 100 will be described as follows.

The components of the inspection apparatus 100, for obtaining optical data of the mask Ma, as one example of the object to be inspected, includes a table 101 that is movable in a horizontal direction (X-direction and/or Y-direction) and a rotational direction ($\theta$-direction), a laser length measuring unit 102 as a position measuring unit that measures position coordinates of the table 101, a light source 105 for emitting light for illuminating a mask Ma, an illumination optical unit for illuminating the light from the light source 105 to the mask Ma positioned on the table 101, and an imaging unit that generates optical image data of the mask Ma. In the mask Ma, a pattern, that is, an object to be inspected (pattern to be inspected) is formed on a principal surface of a transparent substrate, for example, a glass substrate.

The table 101 is controlled by the table control unit 103. Specifically, the table control unit 103 moves the table 101 in the horizontal direction (X-direction and/or Y-direction) and rotational direction (θ-direction) by driving an X-axis motor, a Y-axis motor, and a 0-axis motor (not shown). As examples, an air slider, a linear motor, and a step motor can be used as these driving mechanisms and can further be used in any combination with each other.

The laser length measuring unit 102 is one example of the position measuring unit according to the present invention, and is used for measuring the position coordinate of the table 101. Although a detailed illustration of the laser length measuring unit 102 is omitted, the laser length measuring unit 102 may include a laser interferometer such as a heterodyne interferometer, as one example. The laser interferometer measures position coordinates of the table 101 by illuminating or receiving laser light between each mirror provided along the X-axis and the Y-axis of the table 101. The measured data is sent from the laser length measuring unit 102 to a position information unit 104. A method of measuring the position coordinates of the table 101 is not limited to the method using the laser interferometer, that is, as another example, a method using a magnetic or optical liner encoder can be used.

The illumination optical unit for illuminating the mask Ma, includes half-wavelength plates 106, 111; a polarized beam splitter 107 (first polarized beam splitter); a quarter-wavelength plate 108 (first quarter-wavelength plate); a quarter-wavelength plate 113 (second quarter-wavelength plate); mirrors 109, 110; an objective lens 114; and a polarized beam splitter 112 (second polarized beam splitter). If necessary, the illumination optical unit may include a unit for changing the shape of the light source 105 to a point light source shape or a circular light source shape.

The illumination optical unit according to the present embodiment includes a transmissive illuminating optical unit for illuminating the mask Ma with the light to be transmitted, and a reflective illuminating optical unit for illuminating the mask Ma with the light to be reflected. Referring to FIG. 1, the transmissive illuminating optical unit includes the half-wavelength plate 106, the polarized beam splitter 107 (first polarized beam splitter), the quarter-wavelength plate 108 (first quarter-wavelength plate), and the mirror 109. The reflective illuminating optical unit includes the half-wavelength plate 106, 111, the polarized beam splitter 107 (first polarized beam splitter), the quarter-wavelength plate 113 (second quarter-wavelength plate 113), the mirror 110, the objective lens 114, and the polarized beam splitter 112 (second polarized beam splitter). The half-wavelength plate 106 and the polarized beam splitter 107 (first polarized beam splitter) are common components of the transmissive illuminating optical unit and the reflective illuminating optical unit.

An obtaining unit for generating optical image data of the mask Ma includes an imaging optical unit for imaging an optical image of a pattern disposed in the mask Ma by focusing the light transmitted through or reflected by the mask Ma, a first sensor hereinafter referred to as a TDI sensor 118 for transmission of which light transmitted through the imaging optical unit is incident thereto, for performing photoelectric conversion on the optical image of the pattern of the mask Ma, a second sensor hereinafter referred to as a TDI sensor 119 for reflection, of which light reflected by the mask Ma is incident thereto, for performing photoelectric conversion on the optical image of the pattern of the mask Ma, and a sensor circuit 120 for converting an analogue signal, output from the TDI sensor 118 for transmission and the TDI sensor 119 for reflection, to a digital signal.

The imaging optical unit of the obtaining unit includes an objective lens 114, the quarter-wavelength plate 113, the polarized beam splitter 112, and mirrors 115, 116, and 117. The objective lens 114, the quarter-wavelength plate 113, and the polarized beam splitter 112 are common to the illuminating optical unit.

As the light source 105, for example, a laser light source for emitting DUV (Deep Ultraviolet) light can be used. The light emitted from the laser light source is usually linearly polarized light. According to the present embodiment, the light changed from the linearly polarized light to the circularly polarized light, by the quarter-wavelength plate, is illuminated to the mask Ma. Thereby, an optical image with impartial resolution characteristics is obtained.

The polarized beam splitter 107 (as the first polarized beam splitter) divides the path of the illuminated light emitted from the light source 105 to one light path for illuminating the mask Ma with the light to be transmitted, and another light path for illuminating the mask Ma with the light to be reflected.

In the light path for illuminating the mask Ma with the light to be transmitted, the quarter-wavelength plates 108, 113 are disposed. The quarter-wavelength plate 108 changes the linearly polarized light (p-polarized light) transmitted through the polarized beam splitter 107 to the circularly polarized light, on the other hand, the quarter-wavelength plate changes the circularly polarized light transmitted through the mask Ma to the linearly polarized light (p-polarized light).

The polarized beam splitter 112 as the second polarized beam splitter transmits the linearly polarized light (p-polarized light), transmitted through the quarter-wavelength plate 113, to the obtaining unit. Further, the polarized beam splitter 112 is also disposed along the light path for illuminating the mask Ma with the light to be reflected, and reflects the linearly polarized light (s-polarized light) reflected by the polarized beam splitter 107 to the mask Ma.

The quarter-wavelength plate 113 is also disposed along the light path for illuminating the mask Ma with the light to be reflected, and changes the linearly polarized light (s-polarized light) reflected by the polarized beam splitter 112 to the circularly polarized light. The circularly polarized light reflected by the mask Ma changes to the linearly polarized light (p-polarized light) of which the polarized direction is rotated 90 degrees by transmitting through the quarter-wavelength plate 113 again. Thereby, the light can be transmitted through the polarized beam splitter 112 and continue to the obtaining unit.

The TDI sensor 118 for transmission and the TDI sensor 119 for reflection electrically store a weak expanded optical image of the mask Ma obtained by the imaging optical unit, and convert the optical image to an electric signal of the image and then output the electric signal as the optical image data. The TDI sensor 118 for transmission and the TDI sensor 119 for reflection are area sensors of which an exposure area can be divided into N-sections. The N-sections are provided along the integration direction for accumulating a charge, that is, in order to obtain an optical image of the mask Ma, when the TDI sensor 118 for transmission and the TDI sensor 119 for reflection are scanning the mask Ma, a charge is transferred in every step along the integration direction and the charges corresponding to several accumulated sections are stored and output. Thereby, even if a charge of one section is weak, the output can be obtained by the accumulation of several sections, that is, the addition of sections, wherein the output corresponds to several tens of the light quantity in the case where the addition is not performed, by the same scan time as the time in the case where the addition is not performed. Furthermore, the noise is decreased and the S/N ratio of the image signal is higher by accumulating the same position several times.

The inspection apparatus 100 includes the optical image obtaining unit 121 as a unit for inputting the optical image data output from the sensor circuit 120. Furthermore, the inspection apparatus 100 includes, a line width error obtaining unit 122 as a unit for obtaining a line width error using the optical image data, map generating unit 123 as a unit for generating a ΔCD map from the line width error, a reference image data generating unit 124 for generating the reference image data of the optical image data, a magnetic disk device 125 as one example of a storage device, a magnetic tape device 126 as one example of an auxiliary storage device, a flexible disk device 127 as another example of the auxiliary storage device, a monitor display 128 as one example of a display device, a microscope pattern monitor 129 by an ITV camera as another example of a display device, and a printer 130. Each component is connected to the master control unit 140 controlling the whole of the inspection apparatus 100 through the bus 131 that constitutes a data transmission line. Further, the above-mentioned the table control unit 103 and the position information unit 104 are also connected to the master control unit 140 through the bus 131.

Further, the inspection apparatus 100 includes a comparing unit 133 as a unit for detecting a defect of the mask Ma by comparing the optical image data with the reference image data using a die-to-database comparison method. The comparing unit 133 is one example of a component for detecting a defect in the inspection apparatus 100. Further, the inspection apparatus 100 can also detect a defect by a die-to-die comparison method. In that case, optical image data input to the optical image obtaining unit 121 is compared with each other. It is not necessary for the reference image data to be generated, and further, the inspection apparatus 100 does not need to include the reference image data generating unit 124. The optical image obtaining unit 121 can also be used for detecting a defect, and further, the optical image obtaining unit 121 may be separated into an optical image obtaining unit 121 to obtain optical images, and a unit for detecting a defect, thereby, the optical image data can be transmitted from the optical image obtaining unit 121 to the unit for detecting a defect.

As the inspection apparatus 100 includes the above-mentioned components, the inspection apparatus 100 can generate a ΔCD map by obtaining a line width error of the pattern to be inspected of the mask Ma, and can further detect a defect of the pattern to be inspected.

Next, one example of an inspection method using inspection apparatus 100 shown in FIG. 1 will be described.

Figure 2:
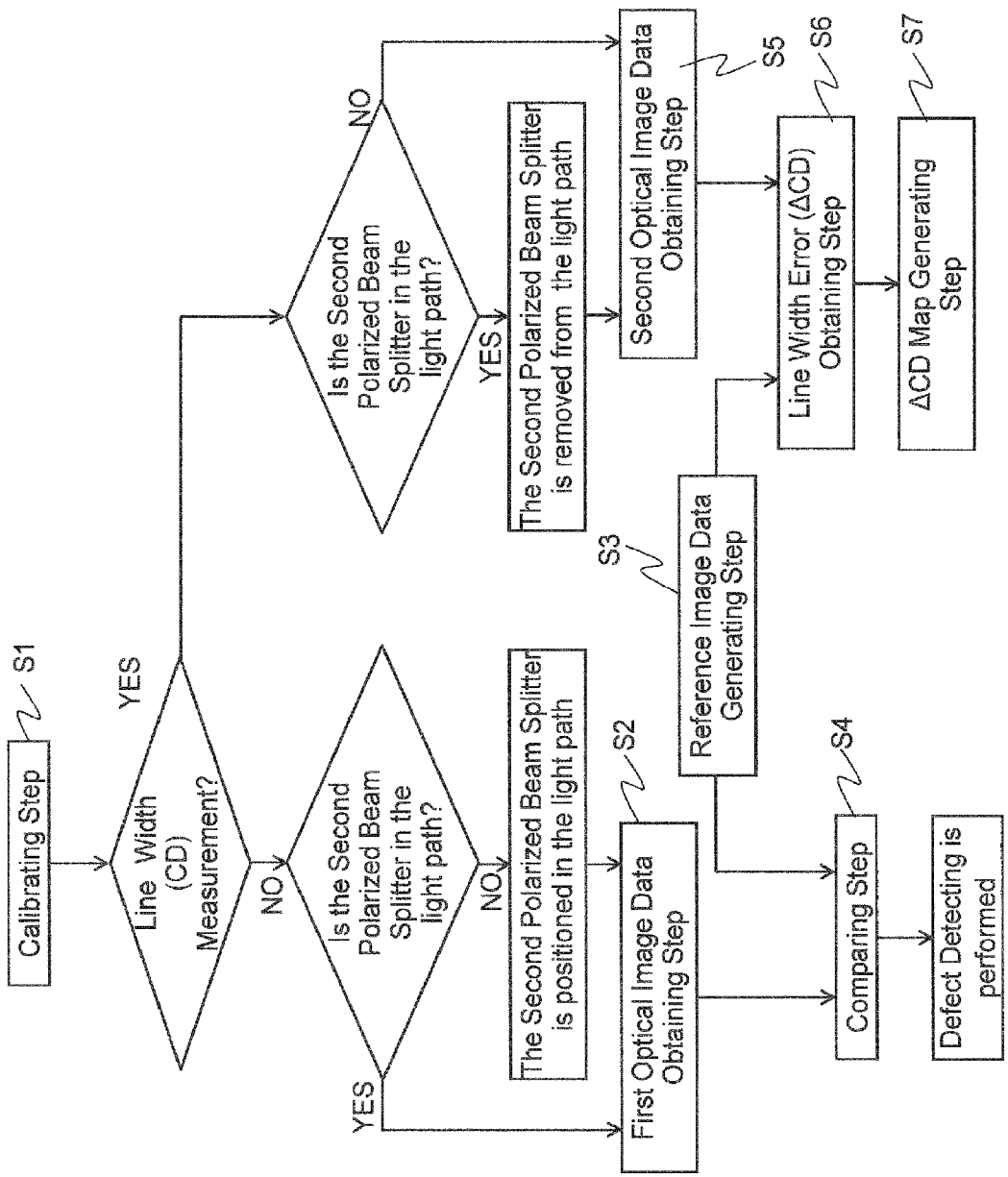
FIG. 2 is one example of a flowchart illustrating the inspection method according to the first embodiment.

FIG. 2 is one example of a flowchart illustrating the inspection method according to the present embodiment. As shown in FIG. 2, the inspection method according to the present embodiment includes a calibrating step (S1), a first optical image data obtaining step (S2), a reference image data generating step (S3), a comparing step (S4), a second optical image data obtaining step (S5), a line width error (ΔCD) obtaining step (S6), and a ΔCD map generating step (S7). The comparing step (S4) is one example of the defect detecting step according to the present invention.

Next, these steps will be described referring to FIG. 1 and FIG. 2.

<Calibrating Step (S1)>

The TDI sensor is constructed by gathering multiple sensor elements. All sensor elements need to have the same electrical characteristics (gain and offset characteristics) because the fluctuation of the characteristics among these sensor elements causes malfunction. Accordingly, before the optical image for detecting a defect and obtaining a line width error is obtained, the TDI sensor 118 for transmission and the TDI sensor 119 for reflection are calibrated. The calibration will be specifically explained below.

The optical image obtained by the TDI sensor 118 for transmission is input to a digital amplifier (not illustrated), provided in the sensor circuit 120, which can adjust an offset and a gain of each pixel. Specifically, the calibrating step is a step for determining the gain of each pixel of the digital amplifier. For example, in the calibrating process step for calibrating the TDI sensor 118 for transmission, the TDI sensor 118 for transmission is disposed at the area where the light is transmitted through the mask Ma, sufficiently wider than an area in which the optical image is obtained by the imaging unit. Next, the optical image of the mask Ma is obtained under the same conditions (for example, the same output of the light source, light quantity of the light source, positions of the various mirrors and lenses, etc.) as the illumination optical unit for illuminating the mask Ma during the inspection, and then a gradation value of the optical image obtained in the imaging area A1, and a gradation value of the optical image obtained in the light quantity fluctuation detecting area A2 are obtained to determine a white level. After the light quantity of the light for illuminating the mask Ma is set to zero, a gradation value of the optical image obtained in the imaging area A1, and a gradation value of the optical image obtained in the light quantity fluctuation detecting area A2 are obtained to determine a black level. At this point, in consideration of a fluctuation in light quantity during the inspection, the offset and gain are adjusted in each pixel such that amplitudes of the white level and black level are distributed in a range of 10 to 240 corresponding to approximately 4% to approximately 94% of 8-bit gradation data.

The optical image data obtained by the TDI sensor 119 for reflection is also input to a digital amp of the sensor circuit 120, and the gain of each pixel of the digital amp is determined by the calibration.

After the calibrating step (S1) is finished, it is determined whether the line width (CD) measurement is to be performed, more specifically, whether the line width measurement or defect detection is performed.

In the present embodiment, in the case where the defect detection is performed without the measurement of a line width error, the polarized beam splitter 112 is disposed along the light path of the illuminating light for transmission as shown in FIG. 1. Specifically, the polarized beam splitter 112 is provided between the quarter-wavelength plate 113 and the TDI sensor 118 for transmission, so that the light transmitted through the mask Ma, the objective lens 114, and further, the quarter-wavelength plate 113, is transmitted through the polarized beam splitter 112, and incident to the TDI sensor 118 for transmission. In this case, the polarized beam splitter 112 is also provided so that the light reflected by the polarized beam splitter 107 is incident to the polarized beam splitter 112. As a result of this light being reflected by the polarized beam splitter 112, the light to be transmitted and the light to be reflected can illuminate the mask Ma at the same time.

On the other hand, in the case where the line width error measurement is performed without the defect detection, the polarized beam splitter 112 is removed from the light path of the illuminating light for transmission. Then, the light transmitted through the quarter-wavelength plate is incident to the TDI sensor 118 for transmission, the line width measurement is then performed using the obtained optical image data.

The reason as to why the polarized beam splitter 112 is removed from the light path of the illuminating light for transmission, in the case where the line width (CD) measurement is performed, will be described.

When the line width (CD) of the pattern to be inspected, formed in the mask Ma, is measured, it is necessary for the position of the edge of the pattern as a reference position of the measurement to be determined. In the present embodiment, the position of the edge is determined by a conventionally known threshold value method. For example, an arbitrary value (threshold value) is specified between the signal amount (brightness) of the black level and the signal amount (brightness) of the white level of the reference image data. The threshold value is a value internally divided between the minimum value and the maximum value of the signal amount by a prescribed division ratio. Then, the position of the edge is set at a position corresponding to the signal amount of the threshold value of the reference image data. Further, the position of the edge is set at a position of the signal amount that corresponds to this threshold value of the optical image data. For example, in the case where the pattern to be inspected is a line-and-space pattern, a threshold value corresponds to the boundary between the line pattern and the space pattern.

Figure 3:
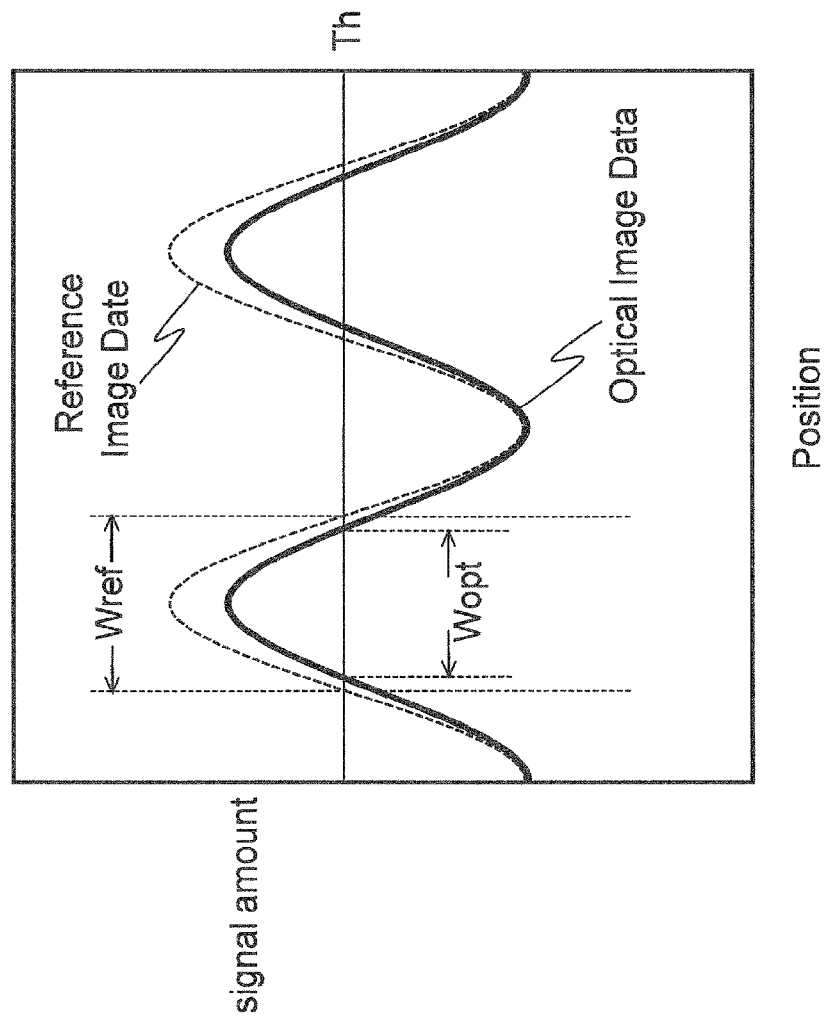
FIG. 3 is one example of a signal amount of optical image data obtained by the TDI sensor for transmission in the configuration in which the polarized beam splitter is disposed along the light path for illuminating light for transmission.

FIG. 3 is one example of a signal amount of optical image data obtained by the TDI sensor 118 for transmission in the configuration as shown in FIG. 1, that is, the configuration in which the polarized beam splitter 112 is provided along the light path of the illuminating light for transmission. In FIG. 3, the horizontal axis illustrates a position on the TDI sensor 118 for transmission. Further, the vertical axis of FIG. 3 illustrates a signal amount of optical image data, and corresponds to a light quantity of the light to be incident to the TDI sensor 118 for transmission. Furthermore, in FIG. 3, the curve illustrated by the dot line is the reference image data. The threshold value Th, for determining the position of the edge of the pattern, is obtained from the reference image data. For example, the threshold value Th is determined by the following formula using the reference image data illustrated by the dot line shown in FIG. 3.

$$Th = \{(\text{Maximum Value of Brightness}) - (\text{Minimum Value of Brightness})\}/2 \quad \text{FORMULA}$$

The position of the edge of the pattern is obtained by determining the threshold value Th, the line width Wref of the pattern is then obtained. The line width Wref corresponds to the design value of the line width of the pattern. A line width error ($\Delta$CD) is obtained by obtaining a difference between the line width Wref and the line width of the optical image data corresponding to the actual pattern (pattern to be inspected). In the optical image data, the edge of the pattern is the position of the signal amount (brightness) equal to the threshold value Th.

The reference image data of the pattern should correspond with the optical image data of the pattern. Accordingly, if a pattern which is exactly the same as the design pattern is formed, the optical image data coincides with the reference image data, and the line width of the pattern of the optical image data will be equal to the line width Wref.

Incidentally, as mentioned above, the substrate consisting of mask Ma has birefringence. As the direction of the birefringence differs depending on the position of the substrate, the polarized state of the light is changed as a result of being transmitted through the mask Ma, that is, the state of the light before transmission changes to a different state after transmission. Thereby, the light quantity of the light transmitted through the polarized beam splitter 112 is decreased. As a result, the light quantity of the light to be incident to the TDI sensor 118 for transmission is decreased. The signal amount of the optical image data is shown by the curve illustrated by the solid line in FIG. 3. Accordingly, when the position of the edge of the pattern of the optical image is determined using the threshold value Th, the line width Wopt is obtained, and as a result, the line width error ($\Delta$CD: Wopt−Wref) is obtained. That is, originally, the line width of the pattern obtained from the optical image data should coincide with Wref, and the line width error $\Delta$CD should be zero. However, it is apparent that a line width error (Wopt−Wref) occurs. As a result, an accurate line width error cannot be obtained.

In the present embodiment, when the line width of the pattern to be inspected of the mask Ma is measured, the polarized beam splitter 112 is removed from the light path of the illuminating light for transmission. Thereby, the decrease of the light quantity of the light transmitted through the mask Ma between the mask and the TDI sensor 118 for transmission can be prevented, and then an accurate line width measurement can be performed.

By removing the polarized beam splitter 112, the mask Ma cannot be illuminated with the light to be reflected. However, when the pattern formed in the mask is transferred to the wafer, the wafer is generally illuminated with the light transmitted through the mask. Therefore, it is of a practical use of the mask Ma that the light transmitted through the mask is incident to the TDI sensor 118 for transmission, and then the line width of the pattern is measured using the obtained optical image data, and the measurement is then fed back to the production process of the mask Ma.

Referring to FIG. 2, after the determination as to whether the measurement of the line width (CD) is performed, in the case where a defect is detected without the measurement of the line width, it is determined whether the polarized beam splitter 112 (the second polarized beam splitter) is disposed along the light path of the illuminating light for transmission and the illuminated light for reflection of the inspection apparatus 100 as shown in FIG. 1. When the polarized beam splitter 112 is not disposed along the light path, the polarized beam splitter 112 can be moved to be disposed along the light path by operating a PBS moving control unit 132.

Figure 4:
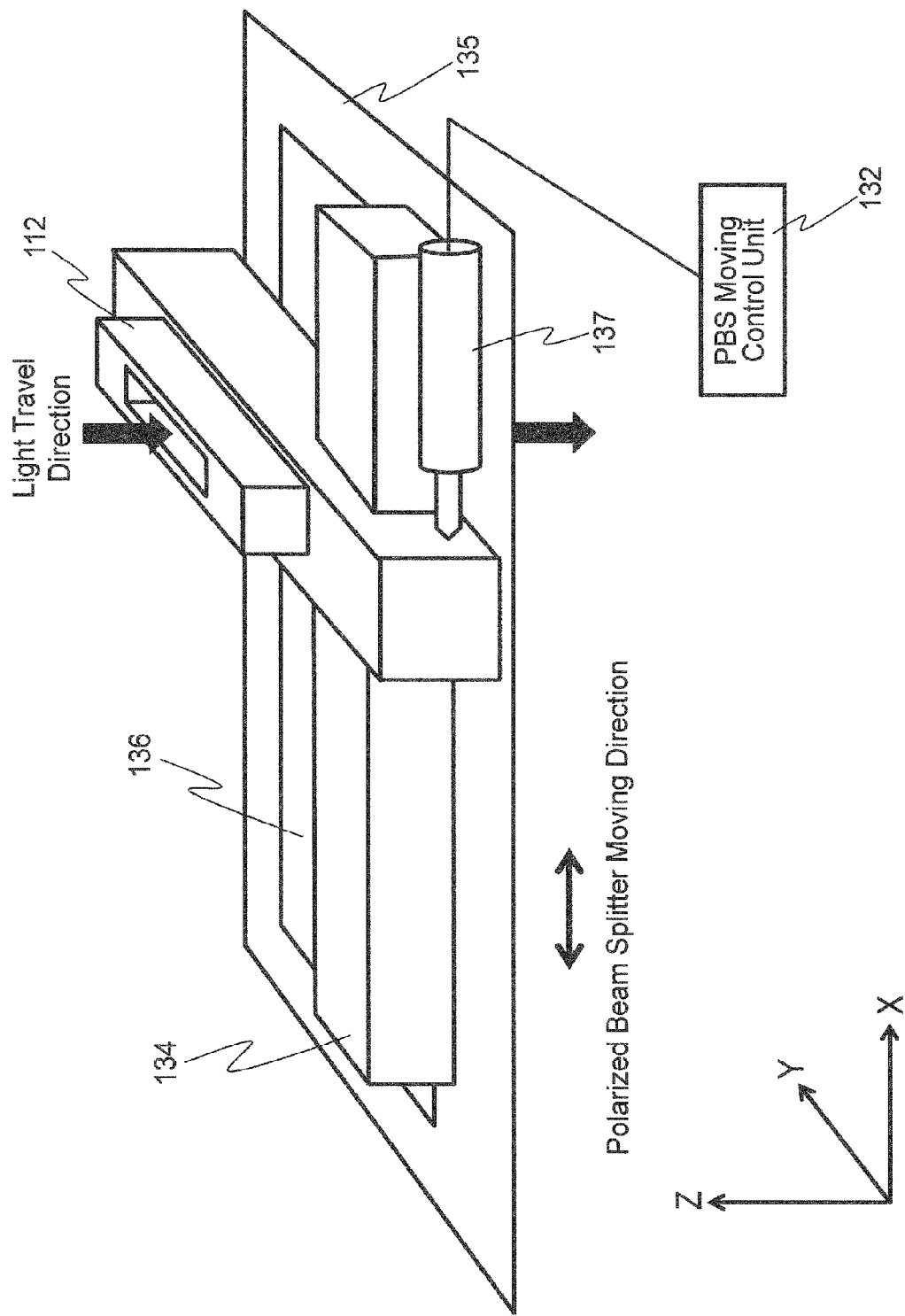
FIG. 4 is a view illustrating the movement of the polarized beam splitter.
Figure 5:
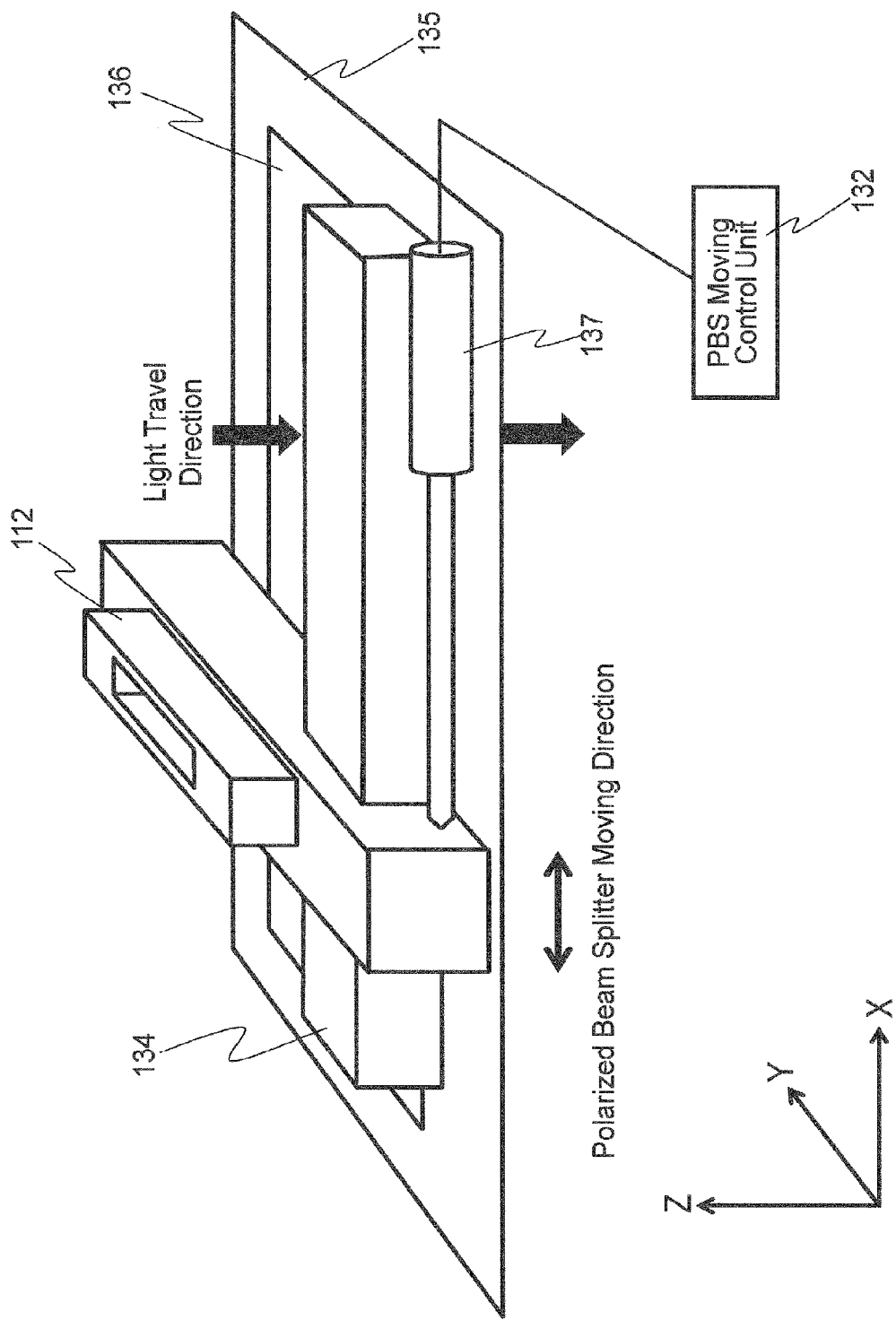
FIG. 5 is another view illustrating the movement of the polarized beam splitter.

The PBS moving control unit 132 shown in FIG. 1 controls the movement of the polarized beam splitter 112 in order to position the polarized beam splitter 112 along the light path of the illuminating light for transmission and the illuminating light for reflection, and remove the polarized beam splitter 112 from the same light path. FIG. 4 and FIG. 5 illustrate the movement of the polarized beam splitter 112. In FIG. 4 and FIG. 5, the polarized beam splitter 112 and a guide 134 are disposed on the pedestal 135. In the pedestal 135 an opening portion 136 for transmitting the light is disposed. The polarized beam splitter 112 can be moved in both the X-direction and the −X-direction under a state where the guide 134 limits the direction of movement. A driving unit using an air cylinder, etc performs this movement. The PBS moving control unit 132 controls the driving unit 137.

The state where the polarized beam splitter 112 (the second polarized beam splitter) is disposed along the light path in FIG. 2 corresponds to the state where the polarized beam splitter 112 is disposed as shown in FIG. 4. The light transmitted through the quarter-wavelength plate 113 in FIG. 4 travels along the −Z-direction as shown in FIG. 4. As the polarized beam splitter 112 is disposed along the light path, the light transmits through the polarized beam splitter 112, and then transmits through the opening portion 136. Further, the light path of the light is bent by the mirrors 115 and 116 as shown in FIG. 1, and is then incident to the TDI sensor 118 for transmission. Alternatively, the light path of the light is bent by the mirrors 115 and 117 and is then incident to the TDI sensor 119 for reflection.

On the other hand, the case where the polarized beam splitter 112 (second polarized beam splitter) is not disposed along the light path in FIG. 2 corresponds to the state where the polarized beam splitter 112 is disposed as shown in FIG. 5. When the detection of a defect is performed by the inspection apparatus 100, in the case that the line width is not measured, the driving unit 137 is operated via the PBS moving control unit 132, so that the polarized beam splitter 112 is disposed along the light path of the light transmitted through the quarter-wavelength plate 113 as shown in FIG. 4.

<First Optical Image Data Obtaining Step (S2)>

When it is confirmed that the polarized beam splitter 112 is disposed along the light path of the light transmitted through the quarter-wavelength plate 113, an optical image of the pattern of the mask Ma is obtained in the first optical image data obtaining step S2.

The mask Ma disposed on the table 101 is fixed on the table 101 using a vacuum chuck device (not shown), as one example. In order to accurately detect a defect of a pattern formed in the mask Ma, and accurately obtain the position of the defect, it is necessary to align the pattern of the mask Ma at the predetermined position on the table 101. Specifically, the X-axis and the Y-axis of the pattern to be measured is matched to the traveling axis of the XY-table in the state where the mask Ma is mounted on the table 101. Therefore, for example, an alignment mark for aligning the position is formed in the mask Ma, and the alignment mark is then obtained by the inspection apparatus 100 to align the pattern of the mask Ma on the table 101. Alternatively, a mask alignment mark may be formed in the mask Ma, thereby the position alignment can be performed using an apex of a corner which is close to the periphery of the mask Ma, and of which the position of the X-coordinate is the same as the Y-coordinate, or the edge of the pattern, in the pattern of the mask Ma.

When the mask Ma is fixed at the predetermined position on the table 101, the light emitted from the light source 105 is illuminated to the pattern formed on the mask Ma through the illumination optical unit. Specifically, the light beam emitted from the light source 105 is transmitted through the half-wavelength plate, and is then divided to one light path for illuminating the mask Ma with the light to be transmitted, and another light path for illuminating the mask Ma with the light to be reflected. In FIG. 1, the solid line illustrates the illuminating light for transmission, and the dot line illustrates the illuminating light for reflection.

The p-polarized light of the linearly polarized light emitted from the light source 105 is transmitted through the polarized beam splitter 107, and is changed to the circularly polarized light by the quarter-wavelength plate 108, the circularly polarized light is then illuminated to the mask Ma. The circularly polarized light is then transmitted through the mask Ma, the objective lens 114, and is changed to the linearly polarized light by the quarter-wavelength plate 113. After that, the linearly polarized light is transmitted through the polarized beam splitter 112 (the second polarized beam splitter), and is then incident to the TDI sensor 118 for transmission by the mirrors 115 and 116.

On the other hand, the s-polarized light of the linearly polarized light emitted from the light source 105 is reflected by the polarized beam splitter 107, and is then incident to the polarized beam splitter 112 via the mirror 110 and the half-wavelength plate 111. As the polarized beam splitter 112 reflects the s-polarized light, the reflected s-polarized light is changed from the linearly polarized light to the circularly polarized light by transmitting through the quarter-wavelength plate 113, the circularly polarized light is then illuminated to the mask Ma through the objective lens 114. Then, the light reflected by the mask Ma is transmitted through the objective lens 114 and the quarter-wavelength plate 113. Thereby, the light is changed from the circularly polarized light to the linearly polarized light, and also becomes the p-polarized light by rotating the direction of the polarized light by 90 degrees. Thereby, the light can transmit through the polarized beam splitter 112. The light is then incident to the TDI sensor 119 for reflection by the mirrors 115 and 117.

As mentioned above, the polarized beam splitter 112 is disposed along the light path of the light transmitted through the mask Ma, and then the light reflected by the polarized beam splitter 107 illuminates to the mask Ma by reflection by the polarized beam splitter 112. Thereby, an optical image by the illumination of the transmitted light, and an optical image by the illumination of the reflected light are simultaneously obtained by illuminating the mask Ma with the light to be transmitted and with the light to be reflected at the same time. That is, the optical image of the pattern to be inspected of the mask Ma can be obtained by illumination of transmitted light by the TDI sensor 118 for transmission, and at the same time, the optical image of the pattern to be inspected can be obtained by illumination of reflected light by the TDI sensor 119 for reflection.

The method for obtaining the optical image of the pattern of the mask Ma of the TDI sensor 118 for transmission and the TDI sensor 119 for reflection (the optical image data obtaining method) will be described as follows. In the present description of the obtaining method, the TDI sensor 118 for transmission is not distinguished with the TDI sensor 119 for reflection, and both sensors are referred to as a TDI sensor.

A region to be inspected in the mask Ma, that is, the region in which a pattern to be inspected is formed is virtually divided into stripe-shaped multiple regions. The stripe-shaped region is called a stripe. Each stripe-shaped region has, for example, a width of several hundred micrometers and a length of about 100 mm that corresponds to a total length in an X-direction or a Y-direction of the region to be inspected.

Further, a plurality of units, each unit represented by "F", in which optical images are obtained (hereinafter each unit is referred to as "frame"), are divided in a grid shape virtually set in each stripe. Each frame is preferably a square having each side equal to the width of the stripe, or a square, wherein each side of the square is the width of the stripe divided into approximately four, that is, the perimeter of the square is equal to the width of the stripe.

Figure 6:
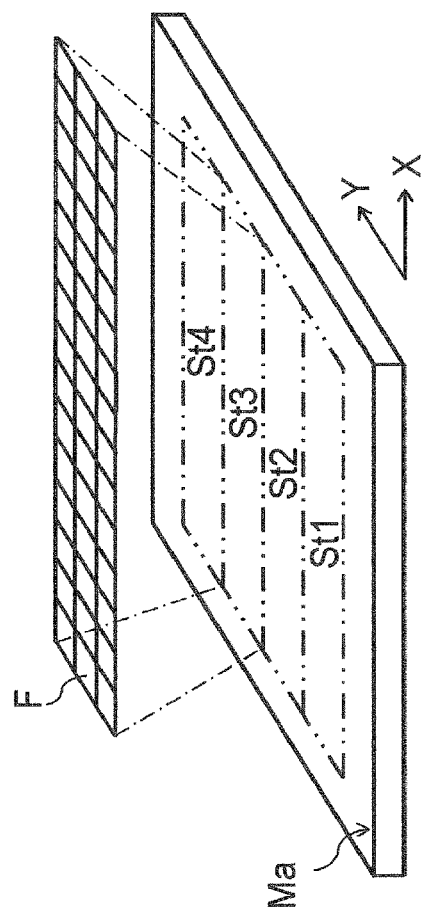
FIG. 6 is a schematic view for illustrating the relationship between the inspection area of the mask, the stripe, and the frame.

FIG. 6 is a schematic diagram explaining a relationship between the area to be inspected of the mask Ma, and the stripes and the frames. In this example, the region to be inspected is hypothetically divided by four stripes ST1 to ST4. Furthermore, in each stripe ST1 to ST4, 45 frames are hypothetically set.

Each stripe ST1 to ST4 has a long shape extending along the X-direction and is arranged along the Y-direction. On the other hand, each frame includes a rectangular shape, for example, a length of one side is several tens of micrometers. In this case, in order to obtain the complete optical image, that is, to prevent the leakage of obtaining the optical image between two frames adjacent frames, the edge of one frame is positioned so that the edge is overlapped to the edge of another frame by a predetermined width. The predetermined width can be a width corresponding to 20 pixels of the TDI sensor, for example. The edges of the adjacent stripes are set so that the edges overlapped each other in the same manner as the frames.

Next, the optical image of the mask Ma is obtained in each stripe. That is, in obtaining the optical image as shown in FIG. 6, the operation of the table 101 is controlled such that each stripe $St_1$, $St_2$, $St_3$, $St_4$, . . . is continuously scanned. Specifically, the optical image of the stripe $St_1$ is sequentially obtained along the X-direction while the table 101 is moved in the −X-direction as shown in FIG. 6. The optical image is continuously input to the TDI sensor. The optical image of the stripe $St_2$ is obtained after the optical image of the stripe $St_1$ is obtained. In this case, after the table 101 moves in the −Y-direction in a stepwise manner, the optical image is obtained while the table 101 moves in the direction (X-direction) opposite to the direction (−X-direction) in which the optical image of the stripe $St_1$ is obtained, and the optical image of the stripe $St_2$ is continuously input to the TDI sensor. When the optical image of the stripe $St_3$ is obtained, after moving the table 101 in the −Y-direction in the stepwise manner, the table 101 moves in the direction opposite to the direction (X-direction) in which the optical image of the stripe $St_2$ is obtained, namely, the direction (−X-direction) in which the optical image of the stripe $St_1$ is obtained. The optical image of the stripe St4 is obtained in the same manner as mentioned above.

In FIG. 1, when the TDI sensor 118 for transmission and the TDI sensor 119 for reflection obtain the optical images of the pattern of the mask Ma, that is, when the optical image data is obtained by converting the optical image of the pattern to an electric signal (analogue signal), the analogue signal of the optical image data is sequentially output to the sensor circuit 120. The sensor circuit 120 converts each analogue signal, output from the TDI sensor 118 for transmission and the TDI sensor 119 for reflection, to a digital signal. Then, the optical image data is output from the sensor circuit 120 to an optical image obtaining unit 121.

<Reference Image Data Generating Step (S3)>

In the reference image data generating step S3 shown in FIG. 2, reference image data is generated based on the design pattern data of the mask Ma in the reference image data generating unit 124 shown in FIG. 1. The detection of a defect of the optical image data is performed based on the reference image data in the comparing step S4 in the inspection by the die-to-database comparison method. Further, the line width, as the basis in the case that the line width error of the pattern of the mask Ma is obtained, is calculated based on the reference image data in the line width error (ΔCD) obtaining step S6.

Figure 7:
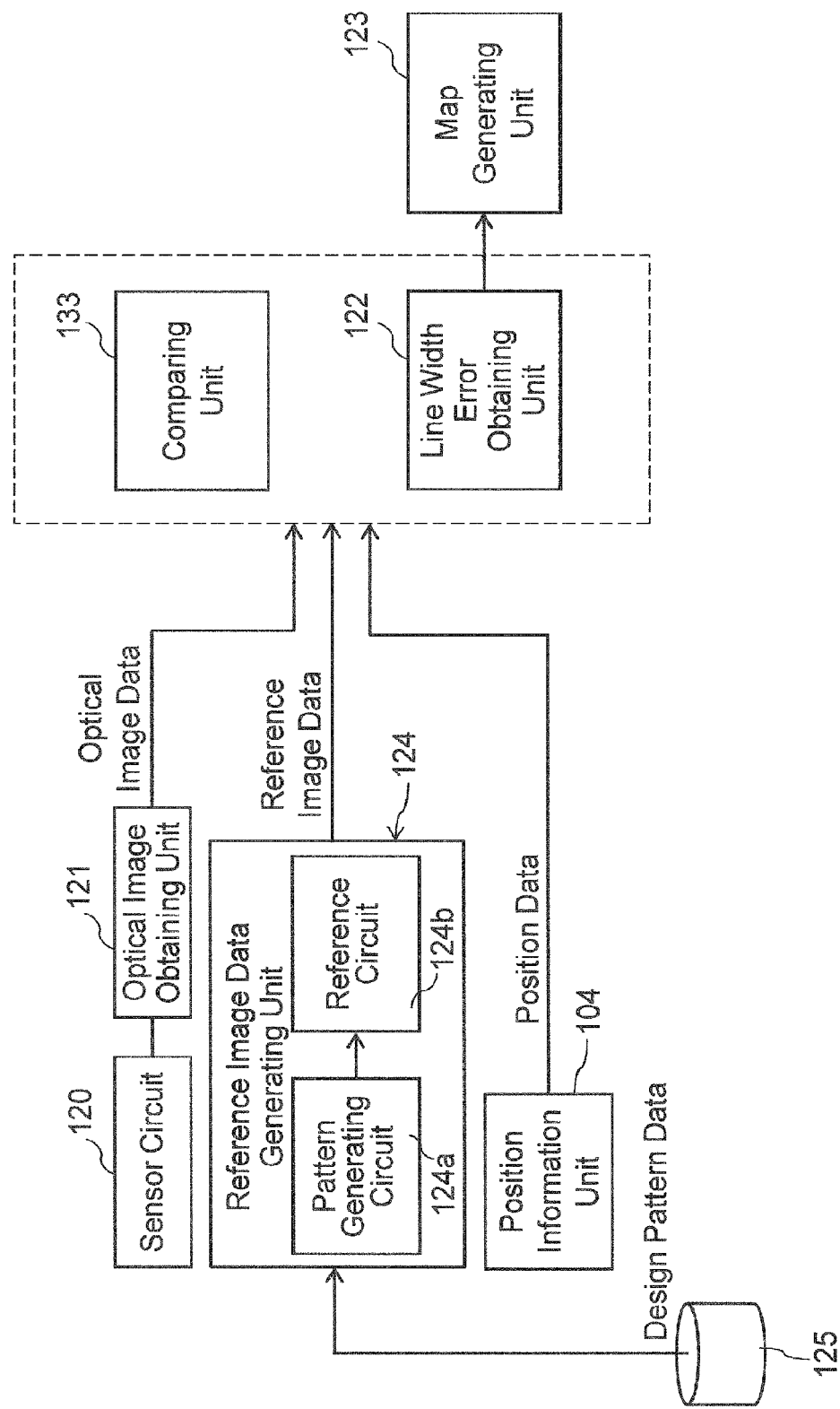
FIG. 7 is a schematic diagram illustrating a flow of data in the inspection apparatus shown in FIG. 1.

FIG. 7 is a schematic diagram illustrating a flow of data in the inspection apparatus 100 shown in FIG. 1. The reference image data generating step S3 will be described referring to FIG. 1 and FIG. 7.

The design pattern data of the mask Ma is stored in the magnetic disk device 125. The design pattern data is read from the magnetic disk device 125, and is then transmitted to the reference image data generating unit 124. The reference image data generating unit 124 includes the pattern generating circuit 124a and the reference circuit 124b. When the design pattern data is input to the pattern generating circuit 124a, the pattern generating circuit 124a converts the design pattern data to a binary or multi-image data. Then, the image data is transmitted from the pattern generating circuit 124a to the reference circuit 124b. In the reference circuit 124b a filter process is performed to the image data. The reason why the filtering process of the image data is performed is as follows.

In the production process, because roundness of a corner and a finished dimension of the line width of the pattern disposed in the mask Ma are generally adjusted, the pattern disposed in the mask Ma does not strictly correspond to the design pattern. Further, the optical image data output from the sensor circuit 120 is faint due to a resolution characteristic of the optical unit or an aperture effect of the TDI sensor 118 for transmission and the TDI sensor 119 for reflection, in other words, the functioning state of a spatial lowpass filter.

Accordingly, a function for generating a reference image, hereinafter referred to as a "reference image generating function", is determined by simulating the fluctuation caused by the production process of the mask Ma and the optical unit of the inspection apparatus 100 based on the design pattern data and the optical image data of the mask Ma. The design pattern data is subjected to a two-dimensional digital filter using the reference image generating function. According to the present embodiment, the reference circuit 124b performs a filtering process to the image data output from the pattern generating circuit 124a, using the reference image generating function, to generate the reference image data.

<Comparing Step (S4)>

In the comparing step S4 shown in FIG. 2, the detection of a defect of the pattern of the mask Ma is performed using the optical image data and the reference image data in the comparing unit 133 shown in FIG. 1.

In the comparing unit 133, optical image data output from the optical image obtaining unit 121 is divided to a predetermined size, for example, frame data size. The reference image data output from the reference image data generating unit 124 is also divided to the frame data size corresponding to the optical image data. As mentioned below, each optical image data divided to frame data size is called optical frame data, and each reference image data divided to frame data size is called reference frame data.

As mentioned below, a defect of the optical frame data is detected by comparing optical frame data to the reference frame data in the comparing unit 133. Further, measurement data, measured by the laser length measuring unit 102, is transmitted from the position information unit 104 to the comparing unit 133, and then position coordinate data of a defect is generated using the measurement data.

The comparing unit 133 includes several tens of comparison parts for processing multiple optical frame data and multiple reference frame data corresponding to each optical frame data, at the same time. After the processing of optical frame data is completed, each comparison part then uses the optical frame data and reference frame data corresponding to optical frame data that has not been processed. Thus, a large amount of optical frame data is sequentially processed as mentioned above and therefore a defect or defects can be detected.

The specific processes performed by the comparison parts are as follows.

Firstly, the optical frame data and the reference frame data, corresponding to the optical frame data, are output to each comparing unit as one set. Then, in the comparing unit, alignment of the reference frame data and the optical frame data (frame alignment) is performed. In this case, the optical frame data and the reference frame data are parallel shifted in a unit of a pixel (of the TDI sensor 118 for transmission and 119 for reflection), so that the position of the edge of the pattern and the position corresponding to the peak brightness position correspond, and the optical frame data and the reference frame data are adjusted less than a size of a unit of a pixel, by prorating the brightness of the neighboring pixel.

After the reference frame data and the optical frame data are aligned, defect detection in accordance with an appropriate comparison algorithm it is performed. For example, evaluation of the level difference between each pixel of the reference frame data and the optical frame data, and a comparison of the differential value of pixels in the pattern edge direction is performed. When the difference between the reference image data and the optical image data exceeds the predetermined threshold value, that position is determined to be defective.

For example, the threshold value that is registered as a line width defect is specified in a unit of a measurement difference (nm), and a measurement ratio (%) of a line width (CD: Critical Dimension) and the critical dimension ratio between the optical image data and the reference image data. Two kinds of threshold values are specified, the measurement difference of the line width is 16 nm and the measurement ratio is 8%, for example. When the line width of the pattern of the optical image data is 200 nm, if the measurement difference between optical image data and the reference image data is 20 nm, it is determined that this pattern has a defect because the value (20 nm) is greater than either the threshold value of the measurement difference and the threshold value of the measurement ratio.

The threshold value of the determination of a defect can be specified separately, in either the case where the line width is thicker than the reference image data, or the case where the line width is thinner than the reference image data. Further, the threshold value can be specified separately, in either the case where the width of the space between lines (the distance between patterns), instead of the line width, is thicker than the reference image data, or the case where the width of the space between the lines (the distance between the patterns), instead of the line width, is thinner than the reference image data. Further, regarding the pattern having a hole shape, a threshold value of the measurement of the diameter of the hole and the threshold value of the measurement ratio of the diameter of the hole can be specified. In this case, the threshold value can be specified for the cross-section of the hole along the X-direction, and a cross-section of the hole along the Y-direction, respectively.

An algorithm used for defect detection, in addition to the above-mentioned may also include, for example, a level comparison method or a differential comparison method. In the level comparison method, for example, the brightness value of the pixel in the optical frame data, namely the brightness value of the region corresponding to the pixel of the TDI sensor 118 for transmission and the TDI sensor 119 for reflection is calculated. Then, the brightness value of the reference frame data and the calculated brightness values are compared, thus, the defect is detected. In the differential comparison method, the direction along the edge of the fine pattern on the optical frame data, for example, the variation in the brightness value of the pixel in the direction along the edge of the line pattern is determined by differentiation. By comparing the variation of the brightness value of the optical data, and the variation of the brightness value of the reference frame data, the defect is detected.

When the comparing unit 133 determines that the optical frame data has a defect, the defect information, such as the optical frame data, the position coordinate data of the defect information of the defect, the compared reference frame data, etc., are registered in the magnetic disk device 125.

The comparing unit 133 performs a plurality of comparison determinations while the condition of the alignment of the frame data is changed. The comparison determination includes the alignment of the frame data, defect detection, and counting the number of defect detections. The comparing unit 133 performs the comparison determination for every set of optical frame data and reference frame data, corresponding to the optical frame data, and for every comparison algorithm. The comparing unit 133 can register the defect detection result having the lowest number of defects detected by the comparison determination in the defect registration unit.

As mentioned above, the optical image data and the reference image data are sequentially input to the comparing unit 133, and a defect detection of the optical image data is performed by comparing the optical image data and the reference image data.

Next, in FIG. 2, after the determination as to whether the measurement of the line width (CD) is performed, the case in which a defect is detected without the measurement of the line width will be described. In this case, the determination as to whether the polarized beam splitter 112 (the second polarized beam splitter) is disposed along the light path of the illuminating light for transmission and the illuminated light for reflection of the inspection apparatus 100 as shown in FIG. 1, is performed. In the case where the polarized beam splitter 112 is disposed, the PBS moving control unit 132 is operated so that the polarized beam splitter 112 is removed from the above-mentioned light path. That is, as shown in FIG. 4, in the case where the polarized beam splitter 112 is disposed along the light path of the light which is travelling along the −Z-direction by transmitting through the quarter-wavelength plate 113, the driving unit 137 is operated via the PBS moving control unit 132, thereby the polarized beam splitter 112 is removed from the light path of the light transmitted through the quarter-wavelength plate 113, as shown in FIG. 5.

<Second Optical Image Data Obtaining Step (S5)>

After it is confirmed that the polarized beam splitter 112 is not disposed along the light path of the light transmitted through the quarter-wavelength plate 113, an optical image of the pattern of the mask Ma is obtained in the second optical image data obtaining step S5.

Figure 8:
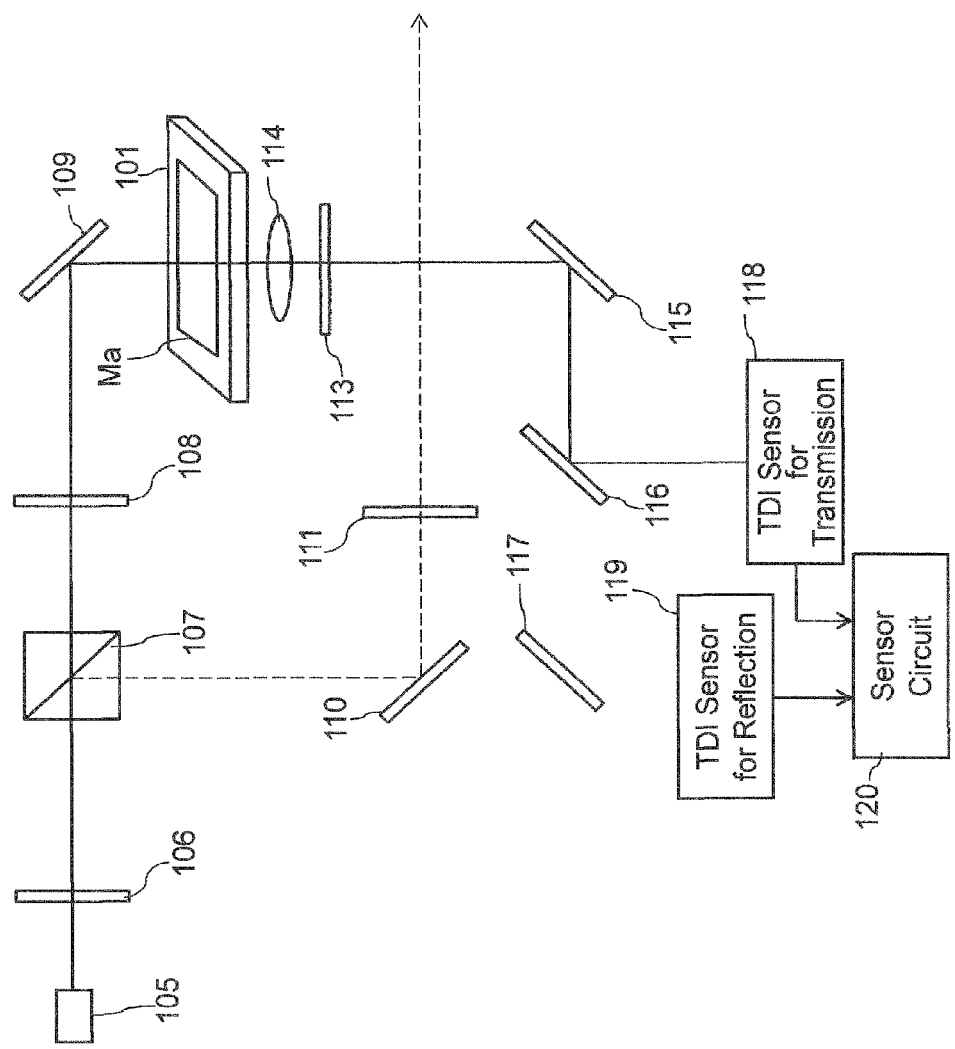
FIG. 8 is a diagram illustrating light paths in the case where the polarized beam splitter is not disposed in FIG. 1.

FIG. 8 is a diagram illustrating the light path in the case where the polarized beam splitter 112 is not disposed in the inspection apparatus 100 according to the present embodiment. In this case, the p-polarized light of the linearly polarized light emitted from the light source 105 is transmitted through the polarized beam splitter 107, and is changed to the circularly polarized light by the quarter-wavelength plate, and is then illuminated to the mask Ma. Then, the light is transmitted through the mask Ma, the objective lens 114, and is changed to the linearly polarized light by the quarter-wavelength plate 113, and is then incident to the TDI sensor 118 for transmission by the mirrors 115 and 116.

On the other hand, the s-polarized light of the linearly polarized light emitted from the light source 105 is reflected by the polarized beam splitter 107, and is then transmitted through the half-wavelength plate 111 by the mirror 110. As the polarized beam splitter 112 is not disposed ahead of the half-wavelength plate 111, the light does not travel to the mask Ma, therefore the mask Ma is not illuminated with the light to be reflected.

As shown in FIG. 8, in the optical unit without the polarized beam splitter 112, the light is incident to only the TDI sensor 118 for transmission, that is, the light is not incident to the TDI sensor 119 for reflection. When the optical image of the pattern of the mask ma is obtained by the TDI sensor 118 for transmission, that is, the optical image data is obtained by converting the optical image of the pattern to an electric signal (analogue signal), analogue signal of the optical image data is sequentially output to the sensor circuit 120. The sensor circuit 120 converts each analogue signal output from the TDI sensor 118 for transmission and the TDI sensor 119 for reflection to a digital signal. Then, the optical image data is output from the sensor circuit 120 to the optical image obtaining unit 121.

<Line Width Error (ΔCD) Obtaining Step (S6)>

As mentioned above, when the line width (CD) of the pattern of the mask Ma is measured, firstly, the position of the edge as a reference position of the measurement is determined. The position of the edge can be determined by a conventionally known threshold value method. For example, an arbitrary value (threshold value Th) is specified between the signal amount (brightness) of the black level and the signal amount (brightness) of the white level of the reference image data. The threshold value Th is a value internally divided between the minimum value and the maximum value of the signal amount by a prescribed division ratio. Then, the position of the edge is set at a position corresponding to the signal amount of the threshold value Th of the reference image data. Further, the position of the edge is set at a position where the signal amount (brightness) corresponds to this threshold value Th of the optical image data. That is, the position of the signal amount corresponding to the threshold value Th should be the edge of the pattern.

After the position of the edge of the pattern is determined, the line width Wref of the pattern of the reference image data can be obtained. The line width Wopt of the pattern of the optical image data corresponding to the reference image data can also be obtained. Accordingly, the line width error (ΔCD) can be obtained by obtaining a difference between Wref and Wopt.

According to the present embodiment, the line width measurement is performed using the optical image obtained in the case where the polarized beam splitter 112 is not disposed. Therefore, even if the polarized state of the light is changed as a result of birefringence of the substrate, consisting of the mask Ma, it is not necessary to consider the decrease of the light quantity due to the polarized beam splitter 112. Accordingly, the line width measurement can be accurately performed, and as a result, a correct line width error can be obtained.

The line width is specifically obtained as follows.

Firstly, the optical image data is transmitted from the optical image obtaining unit 121 to the line width error obtaining unit 122. The reference image data is transmitted from the reference image data generating unit 124, to the line width error obtaining unit 122. In the line width error obtaining unit 122, an edge pair which is a reference of line width (CD) measurement, is detected in the optical image data and the reference image data respectively. Specifically, each position of the edge of the reference image data and the optical image data is detected using the above-mentioned threshold value. Among the detected edges, one edge, which is a starting point of the line width measurement, and another edge, which is an ending point of the same line width measurement compose the edge pair. The edge pair is detected in a unit of a pixel, for example. For example, in the case where the line pattern consists of two edges extending along the Y-axis, an edge pair is detected in a unit of a pixel on both edges. Further, in the case where the pattern is a line pattern consisting of two edges extending along the X-axis, an edge pair is also detected in a unit of a pixel on both edges.

The detection of the edge pair is performed in the line width error obtaining unit 122. The measurement value of the position coordinate of the table 101, measured by the laser length measuring unit 102, is transmitted from the position information unit 104 to the line width error obtaining unit 122. Thereby, a position coordinate of each edge is obtained. Specifically, this process will be described as follows. Firstly, optical image data obtained in a unit of a stripe is divided into data of a predetermined size, for example, data of a unit of a frame. Next, a predetermined region of optical image data is compared with reference image data corresponding to the predetermined region, and the table 101 is then moved in parallel to a position at which an absolute value of a difference between the optical image data and the reference image data becomes the minimum, or a position at which the sum of squares of the difference between the optical image data and the reference image data becomes the minimum, using a pattern matching method. A position coordinate of the pattern to be measured is determined from the amount of the parallel movement, and from the data of the laser length measuring unit 102 corresponding to the frame. The position coordinate of the edge can thereby be obtained.

After the edge pair is detected, the line width error is obtained in the line width error obtaining unit 122.

As one example of a pattern to be measured, the pattern is a line-and-space pattern of which each line pattern consisting of two edges extending along the Y-direction are arranged along the X-direction at predetermined intervals so that a plurality of space patterns are formed. A line width error regarding the line width of the line pattern, and a line width error regarding the line width of the space pattern are individually measured. Specifically, the line widths of each line pattern and the line widths of each space pattern are measured using the detected edge pairs.

Figure 9:
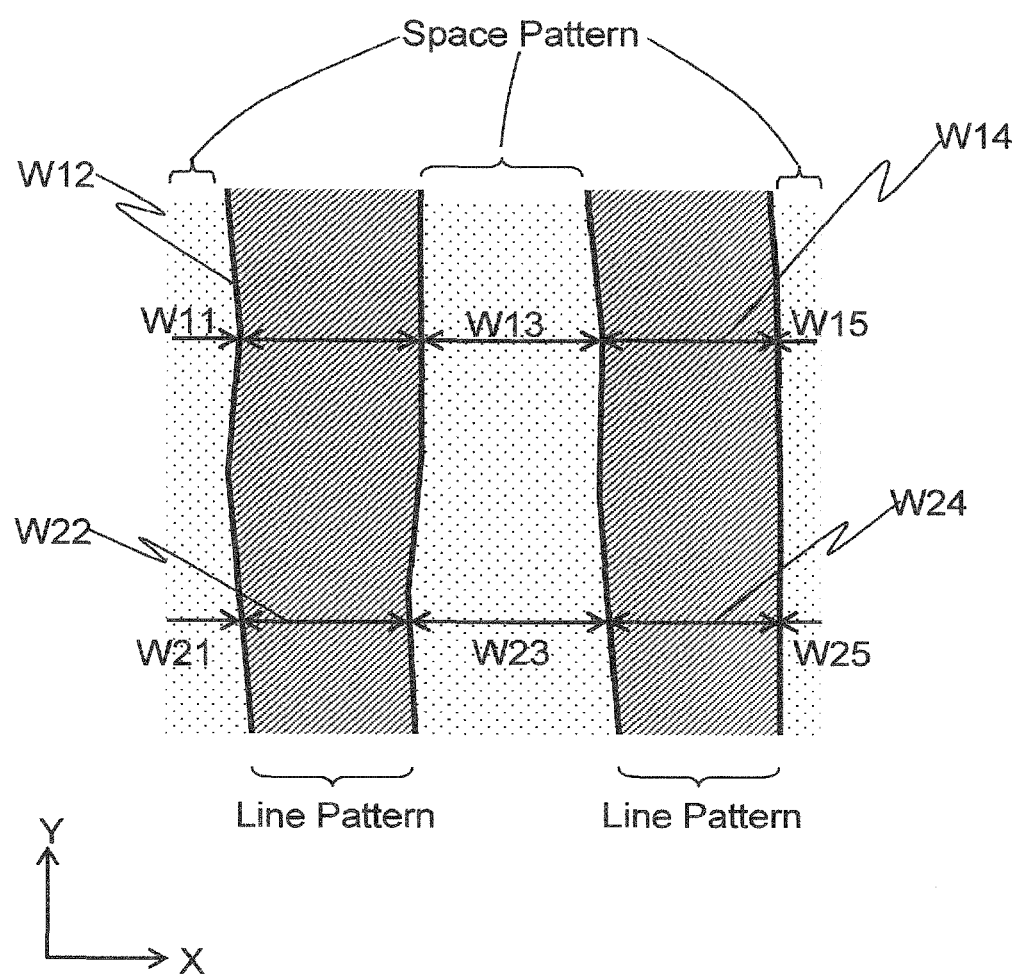
FIG. 9 is a partial plan view of the line-and-space pattern.

FIG. 9 is a plan view of a portion of a line-and-space pattern, as an example of a pattern to be measured. In FIG. 9, the portion indicated by the hatched lines corresponds to the line pattern, and the section provided between two line patterns corresponds to the space pattern. For example, the line widths W12, and W14, etc., are measured along the X-direction at the same position of the Y-direction corresponding to each line pattern. In the same manner, the line widths W11, W13, and W15, etc., are measured along the X-direction corresponding to each space pattern. Then, at the next position, shifted by one pixel in the −Y-direction, the line widths W22, and W24, etc., are measured along the X-direction at the same position of the Y-direction corresponding to each line pattern. In the same manner, the line widths W21, W23, and W25, etc., are measured along the X-direction corresponding to each space pattern.

Figure 10:
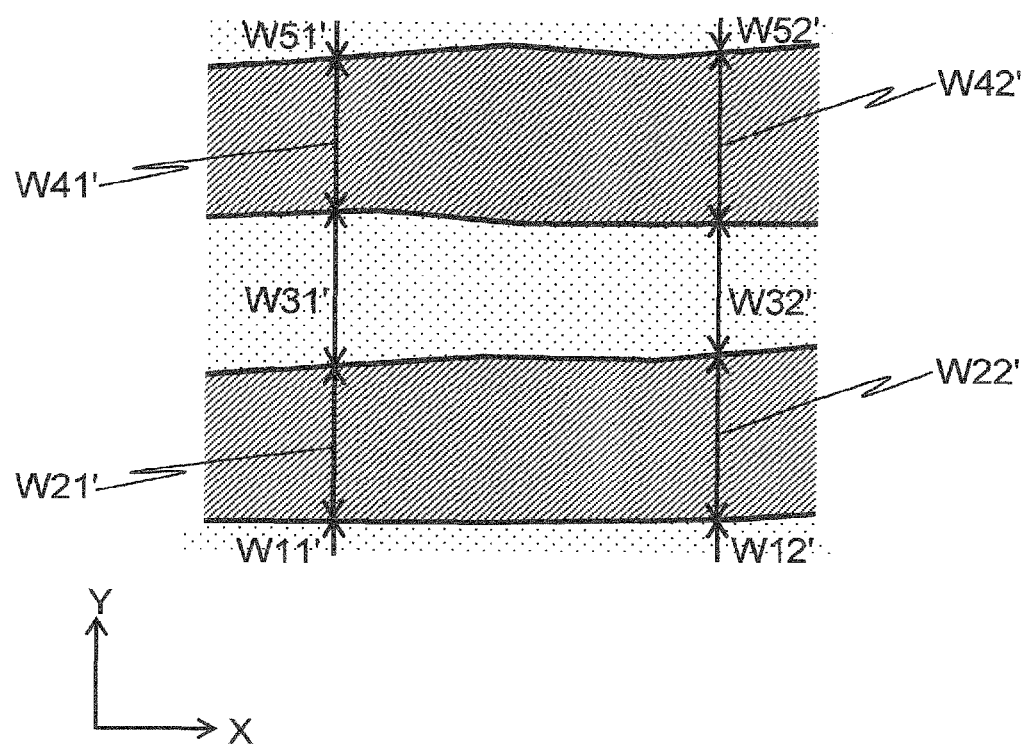
FIG. 10 is another example of the partial plan view of the line-and-space pattern.

FIG. 10 is a plan view of a portion of a line-and-space pattern. In FIG. 9, the portion indicated with the hatched lines corresponds to the line pattern, and the section provided between two line patterns corresponds to the space pattern, in the same manner as in FIG. 9. As shown in FIG. 10, the pattern is a line-and-space pattern of which each line pattern consisting of two edges extending along the X-direction, are arranged along the Y-direction at predetermined intervals so that a plurality of space patterns are formed. In this case, a line width error regarding the line width of the line pattern, and a line width error regarding the line width of the space pattern are also measured individually. That is, the line widths of each line pattern and the line widths of each space pattern are measured using the detected edge pairs.

Specifically, the line widths W21', and W41', etc., are measured along the Y-direction at the same position as the X-direction corresponding to each line pattern. In the same manner, the line widths W11', W31', and W51', etc are measured along the Y-direction corresponding to each space pattern. Then, at the next position, shifted by one pixel in the X-direction, the line widths W22', and W42', etc are measured along the Y-direction at the same position as the X-direction corresponding to each line pattern. In the same manner, the line widths W12', W32', and W52', etc are measured along the Y-direction corresponding to each space pattern.

These line widths measured by the above-mentioned method corresponding to each pattern are compared to line widths obtained using edge pairs of the reference image data corresponding to edge pairs of the optical image data to obtain the difference. The obtained difference is a line width error ($\Delta CD$). The line width error is obtained in each frame, for example. In the example shown in FIG. 9, and the example shown in FIG. 10, the line width errors along the X-direction, and the line width errors along the Y-direction are obtained using the measurement values, in each frame corresponding to the line pattern. In the same manner, the line width errors along the X-direction, and the line width errors along the Y-direction are obtained, using the measurement values, in each frame corresponding to the space pattern.

<$\Delta CD$ Map Generating Step (S7)>

The $\Delta CD$ map generating step (S7) shown in FIG. 2, is performed in the map generating unit 123 shown in FIG. 1. Specifically, the value of the line width error ($\Delta CD$) and the measurement value of the position coordinate of the table 101 (transmitted from the position information unit 104) are transmitted from the line width error obtaining unit 122 to the map generating unit 123. The map generating unit 123 generates a $\Delta CD$ map by associating the line width error ($\Delta CD$) with the position coordinate on the mask Ma.

For example, a whole pattern to be measured is divided into a plurality of unit regions consisting of a predetermined region, and a plurality of regions surrounding the predetermined region, of which each surrounding region has the same size as the predetermined region. Then, the minimum value of an absolute value of a difference ($\Delta CD$) between the line width of the predetermined region of the optical image of the pattern to be measured and the line width of the region of the reference image corresponding to the predetermined region, or the minimum value of the sum of squares of the difference ($\Delta CD$) between the line width of the predetermined region of the optical image of the pattern to be measured and the line width of the region of the reference image corresponding to the predetermined region, is obtained in every unit region. Further, in regards to regions surrounding the predetermined region, of which each region has the same size as the predetermined region, an absolute value of a difference ($\Delta CD$) between the line width of the predetermined region of the optical image of the pattern to be measured and the line width of the region of the reference image corresponding to the predetermined region becomes the minimum, or a position at which the sum of squares of the difference ($\Delta CD$) between the line width of the predetermined region of the optical image of the pattern to be measured and the line width of the region of the reference image corresponding to the predetermined region becomes the minimum, is obtained in every region. Then, an average value of the minimum values of those regions, that is, the predetermined region and a plurality of regions surrounding the predetermined region, is obtained, and the average value becomes an average of $\Delta CD$ in every region. A map is generated by correlating the average of $\Delta CD$ and the position coordinate on the mask Ma. The unit region can be a frame, as one example.

As mentioned above, according to the present embodiment, in the case where an inspection for detecting a defect is performed, the polarized beam splitter is disposed along the light path of the light transmitted through the mask, and the light reflected by the polarized beam splitter then illuminates the mask. Accordingly, the mask can be illuminated with the light to be transmitted and with the light to be reflected at the same time, thereby the optical image data obtained by the illuminating light for transmission and the optical image data obtained by the illuminating light for reflection can be obtained at the same time. Among possible defects, there are defects which are difficult to detect by using only one of the illuminating light for transmission or the illuminating light for reflection. However, by performing both illuminations an accurate inspection can be performed in a short period of time.

On the other hand, the measurement of a line width is greatly influenced by a phenomenon in that a light amount is decreased by the polarized beam splitter due to the birefringence of the substrate consisting of the mask. In the case where measurement of a line width is performed, the polarized beam splitter is removed from the light path of the light transmitted through the mask, and then an optical image can be obtained. Thereby, the above-mentioned problem can be resolved and an accurate line width can be obtained. Further, an accurate line width error can be obtained from the line width, thereby, an accurate $\Delta CD$ map can be obtained. In the present embodiment, a $\Delta CD$ map is generated by the inspection apparatus 100. However, an external device of the inspection apparatus 100, using the line width error obtained by the inspection apparatus 100, may also generate the $\Delta CD$ map.

As mentioned above, the configuration of the optical unit is changed depending on the specific case, that is, in the case where the inspection for detecting a defect is performed, or in the case where the measurement of a line width is performed. According to the present embodiment, it is not necessary to obtain the brightness distribution data for every lot as disclosed in the Document 1 (Japanese Unexamined Patent Application Publication No: 2012-220388), and therefore it takes less time to obtain the optical image data.

Second Embodiment

Figure 11:
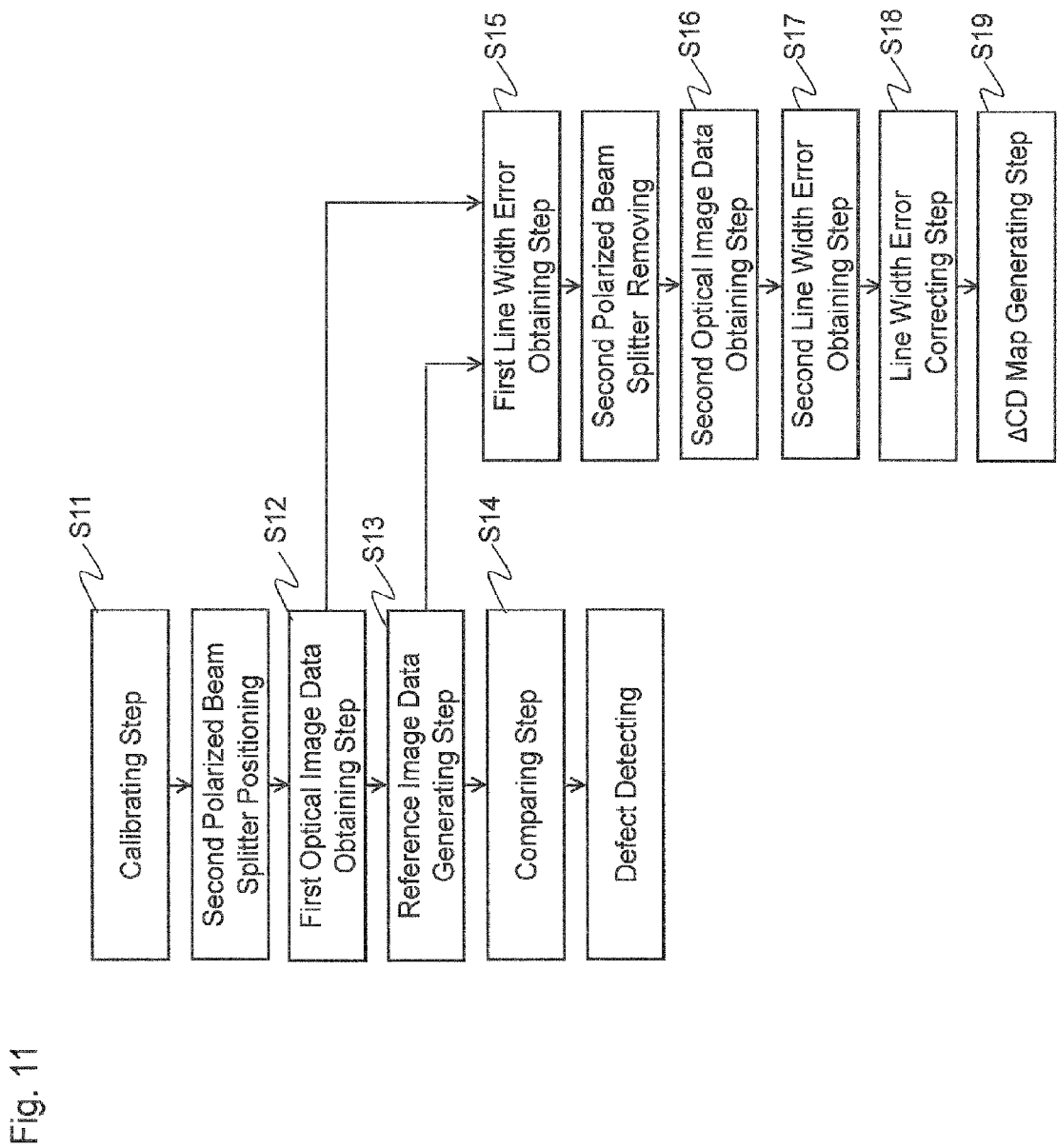
FIG. 11 is a flowchart of the inspection method according to the second embodiment.

FIG. 11 is a flowchart of the inspection method according to the present embodiment. As shown in FIG. 11, the inspection method according to the present embodiment includes a calibrating step S11, a first optical image data obtaining step S12, a reference image data generating step S13, a comparing step S14, a first line width error obtaining step S15, a second optical image data obtaining step S16, a second line width error obtaining step S17, a line width error correcting step S18, and a ΔCD map generating step S19. The comparing step S14 is one example of the defect detecting step according to the present invention.

The inspection method according to the present embodiment can also be performed using the inspection apparatus 100 as shown in FIG. 1 and described in the first embodiment. The inspection method according to the present embodiment will be described as follows referring to FIG. 1, FIG. 11, etc.

<Calibrating Step (S11)>

The explanation of the calibrating step S11 shown in FIG. 11 is omitted as it is the same as the calibrating step S1 shown in FIG. 2, and described in the first embodiment.

<First Optical Image Data Obtaining Step (S12)>

After the calibrating step S1, shown in FIG. 1, the polarized beam splitter 112 (the second polarized beam splitter) is disposed along the light path of the light transmitted through the mask Ma, so that the mask Ma is illuminated with the reflected light by the polarized beam splitter 112, wherein the reflected light is reflected by the polarized beam splitter 107 (the first polarized beam splitter). Then, in this state, the optical image of the pattern of the mask Ma is obtained to obtain the optical image data in the first optical image data obtaining step S12. This step is the same as the first optical image data obtaining step S2 described in the first embodiment.

That is, the linearly polarized light emitted from the light source 105 shown in FIG. 1, is divided to two light paths by the polarized beam splitter 107 (the first polarized beam splitter). Then, after the mask Ma is illuminated with the light transmitted through the polarized beam splitter 107, the light transmitted through the mask Ma is further transmitted through the polarized beam splitter 112 (the second polarized beam splitter), so that the light is incident to the TDI sensor 118 for transmission to obtain the optical image of the mask Ma. On the other hand, the light reflected by the polarized beam splitter 107, is further reflected by the polarized beam splitter 112 to be illuminated to the mask Ma. Further, the direction of the polarized light reflected by the mask Ma is rotated 90 degrees by twice transmitting through the quarter-wavelength plate 113. Thereby, the light transmitted through the polarized beam splitter 112, is incident to the TDI sensor 119 for reflection to obtain the optical image of the mask Ma.

As mentioned above, when the optical images of the pattern of the mask Ma are obtained by the TDI sensor 118 for transmission and the TDI sensor 119 for reflection, that is, when the optical image data is obtained by converting the optical images of the pattern to electric signals, the analogue signals of the optical image data is sequentially output to the sensor circuit 120. The sensor circuit 120 converts each analogue signal output from the TDI sensor 118 for transmission and the TDI sensor 119 for reflection to digital signals respectively. The optical image data is then output from the sensor circuit 120 to the optical image obtaining unit 121.

<Reference Image Data Generating Step (S13)>

In the reference image data generating step S13, reference image data corresponding to the optical image data of the mask Ma is generated. The reference image data generating step S13 is the same as the reference image data generating step S3 described in the first embodiment, and is performed in the reference image data generating unit 124 shown in FIG. 1. The reference image data generating step S13 can be performed before the first optical image data obtaining step S12. Further, the first optical image data obtaining step S12 can be performed in parallel with the reference image data generating step S13.

<Comparing Step (S14)>

In the comparing step S14, a detection of a defect of the pattern of the mask Ma is performed using the optical image data and the reference image data. The comparing step S14 is the same as the comparing step S4 described in the first embodiment, and is performed in the comparing unit 133 shown in FIG. 1. In the comparing unit 133, several tens of comparing parts (not shown) are provided, and optical frame data is simultaneously compared with reference frame data, corresponding to the optical frame data, in parallel. As a result of the comparison, in the case where an existence of a defect of the optical frame data is determined, information of the defect, for example, the optical frame data, the position coordinate frame data of the defect, and the reference frame data compared with the optical frame data are registered in the magnetic disk device 125.

In the present embodiment, a defect can be detected by the die-to-die comparison method. In this case, the optical image data input to the optical image obtaining unit 121 is compared with each other. It is not necessary to generate reference image data, and the inspection apparatus 100 does not necessarily need to include the reference image data generating unit 124. The optical image obtaining unit 121 can also be used for detecting a defect, and further, a unit for detecting a defect can be disposed by separating the optical image obtaining unit 121, thereby, the optical image data can be transmitted from the optical image obtaining unit 121 to the unit for detecting a defect.

<First Line Width Error Obtaining Step (S15)>

In the present embodiment, using the optical image data obtained in the first optical image data obtaining step S12, that is, the optical image data obtained by the TDI sensor 118 for transmission in the state where the polarized beam splitter 112 (second polarized beam splitter) is disposed along the light path, a first line width error ΔCD1 of the pattern to be inspected of the mask Ma is obtained. With the exception of the use of the optical image data obtained in the state where the polarized beam splitter 112 is disposed along the light path, the first line width error obtaining step S15 is the same as the line width error (ΔCD) obtaining step S6 described in the first embodiment.

As mentioned above, in the state where the polarized beam splitter 112 is disposed, the polarized state of the light is changed by the birefringence of the substrate consisting of the mask Ma, thereby, the light quantity of the light for transmission through the polarized beam splitter 112 is decreased. Accordingly, it is impossible to accurately detect an edge of the pattern to be inspected, thereby an accurate line width error cannot be obtained. This problem will be described in detail with reference to FIG. 12.

Figure 12:
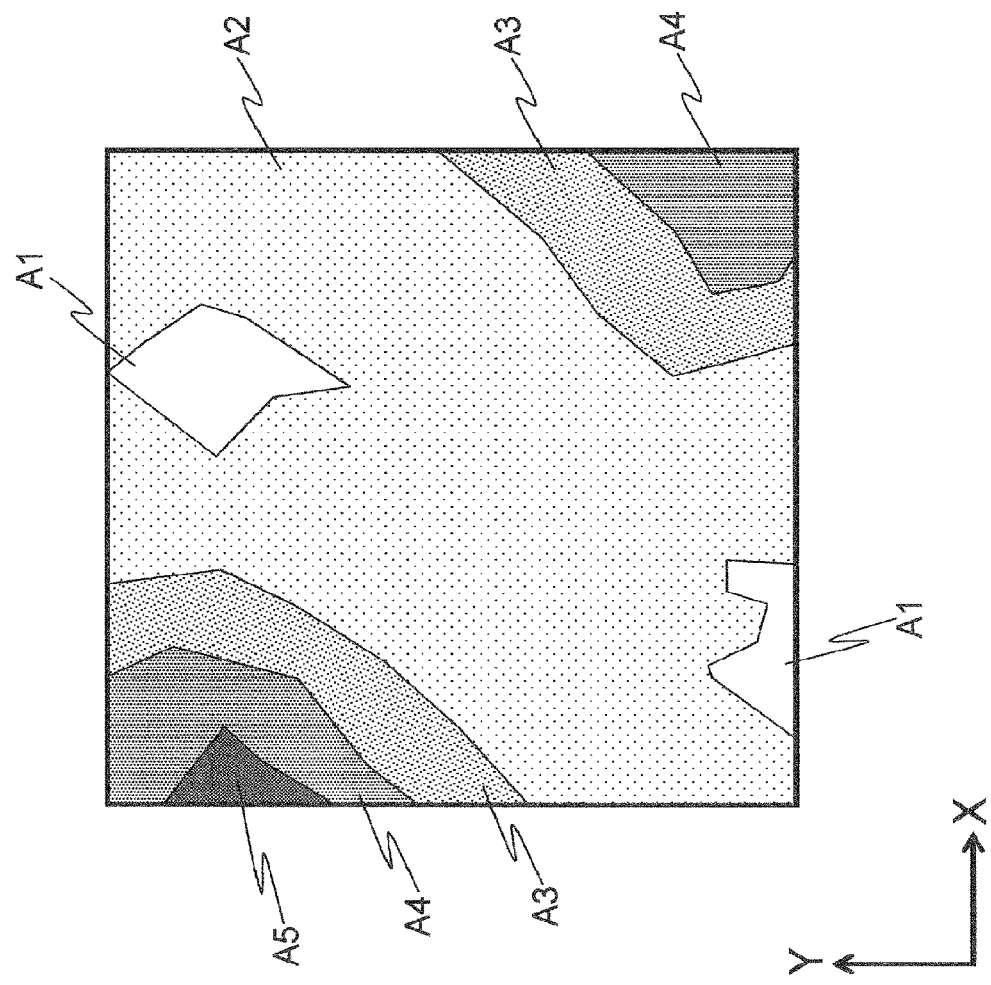
FIG. 12 illustrates the distribution of the light quantity of the light transmitted through the polarized beam splitter, based on the mask in FIG. 1.

FIG. 12 illustrates the distribution of the light quantity of the light transmitted through the polarized beam splitter, based on the mask of FIG. 1. The horizontal axis of FIG. 12 corresponds to a position on the mask Ma along the X-direction. The vertical axis of FIG. 12 corresponds to a position of the mask Ma along the Y-direction.

If the mask Ma does not have birefringence, the light quantity should be uniformly observable in any position. However, a distribution of the light quantity caused by the birefringence is generated after the light is transmitted through the polarized beam splitter 112 as shown in FIG. 12, as one example. In the example shown in FIG. 12, there are five regions, A1 to A5 each of which having a different light quantity. The region A1 is the brightest, and the regions A2, A3, A4, and A5, decrease in brightness in order from A1 to A5.

When the light quantity of the region A2 matches to the light quantity at any position on the mask Ma, in the region A1, of which the light quantity is larger than the region A2, the line width is measured as a larger value than the actual value. On the other hand, in the regions A3, A4, and A5, of which the light quantities are smaller than the region A2, the line widths are measured as smaller values than actual values. Among these line widths, the line width of the region A5 is the smallest line width. That is, if the pattern to be inspected of the mask Ma has a line width according to the design value at any position on the mask Ma, the line width error should be zero. However, if the measurement value of the line width of the region A1 is larger than the actual value, the line width error should be positive. On the other hand, if measurement values of the line width of the regions A3, A4, and A5 are smaller values than the actual values, the line width errors are negative. As a result, a difference between a line width error obtained from a measurement value and an actual line width error (zero in the above-mentioned example) is larger in order from A3 to A5.

In FIG. 11 the first line width error $\Delta CD1$ obtained in the first line width error obtaining step S15, includes an error caused by the light quantity distribution shown in FIG. 12. Accordingly, in the present embodiment, an optical image of the same pattern to be inspected, as the pattern which is obtained in the first optical image data obtaining step S12, is re-obtained in the state where the polarized beam splitter 112 (second polarized beam splitter) is removed from the light path in the second optical image data obtaining step S16. Specifically, the polarized beam splitter 112 is removed from the light path of the light transmitted through the mask Ma, and the optical image data of the mask Ma is then re-obtained in the second optical image data obtaining step S16. The first line width error $\Delta CD1$ obtained in the first line width error obtaining step S15 is then corrected using the second line width error $\Delta CD2$ obtained from the optical image data of the second optical image data obtaining step S16.

<Second Optical Image Data Obtaining Step (S16)>

The second optical image data obtaining step S16 is the same as the second optical image data obtaining step S5 described in the first embodiment. That is, the step of S16 is performed using the optical unit shown in FIG. 8, and described in the first embodiment.

Specifically, the light emitted from the light source 105, transmitted through the polarized beam splitter 107, and then illuminated to the mask Ma, is transmitted through the mask Ma, the objective lens 114, and the quarter-wavelength plate 113, and then is incident to the TDI sensor 118 for transmission by the mirrors 115 and 116. As the polarized beam splitter 112 is not disposed along the light path, the light transmitted through the quarter-wavelength plate 113 is incident to the TDI sensor 118 for transmission without transmitting through the polarized beam splitter 112. The light emitted from the light source 105, reflected by the polarized beam splitter 107, does not travel to the mask Ma because the polarized beam splitter 112 is not disposed in the light path, therefore the mask Ma is not illuminated with the light to be reflected.

<Second Line Width Error Obtaining Step (S17)>

The second line width error $\Delta CD2$ of the pattern to be inspected of the mask Ma is obtained using the optical image data obtained in the second optical image data obtaining step S16, that is, the optical image data obtained by the TDI sensor 118 for transmission in the state where the polarized beam splitter 112 (second polarized beam splitter) is not disposed along the light path. The second line width error obtaining step S17 is the same as the line width error ($\Delta CD$) obtaining step S6 described in the first embodiment, with the exception that the number of positions for measuring line widths are decreased as described below.

In the line width error ($\Delta CD$) obtaining step S6 in the first embodiment, and the first line width error obtaining step S15 of the present embodiment, the measurement points necessary for generating a $\Delta CD$ map, that is, measurement points of the line width necessary for obtaining the line width error to be detected as a defect of the pattern to be inspected, are set. For example, the measurement points of the line width in step S6 and step S15 are set for every pixel. In this case, an edge pair is detected for every pixel, and a line width is measured using the detected edge pair.

On the other hand, in the second line width error obtaining step S17 according to the present embodiment, it is satisfactory that the measurement points for correcting the distribution (fluctuation) of the light quantity, caused by the decrease of the light quantity by the polarized beam splitter 112, are set in a necessary and sufficient manner. When the fluctuation of the light quantity caused by the decrease of the light quantity corresponds to the mask Ma, the fluctuation can be recognized at a plurality of regions on the mask Ma as shown in FIG. 12. That is, the frequency of the fluctuation of the light quantity on the mask Ma is larger than the frequency of the fluctuation of the line width error which is detected as a defect of the pattern to be inspected. Accordingly, for example, the line width is measured in every pixel in the first line width error obtaining step S15, whereas in the second line width error obtaining step S17, the measurement of the line width can be performed in a unit which is larger than the pixel unit of the first line width error obtaining step S15.

Figure 13:
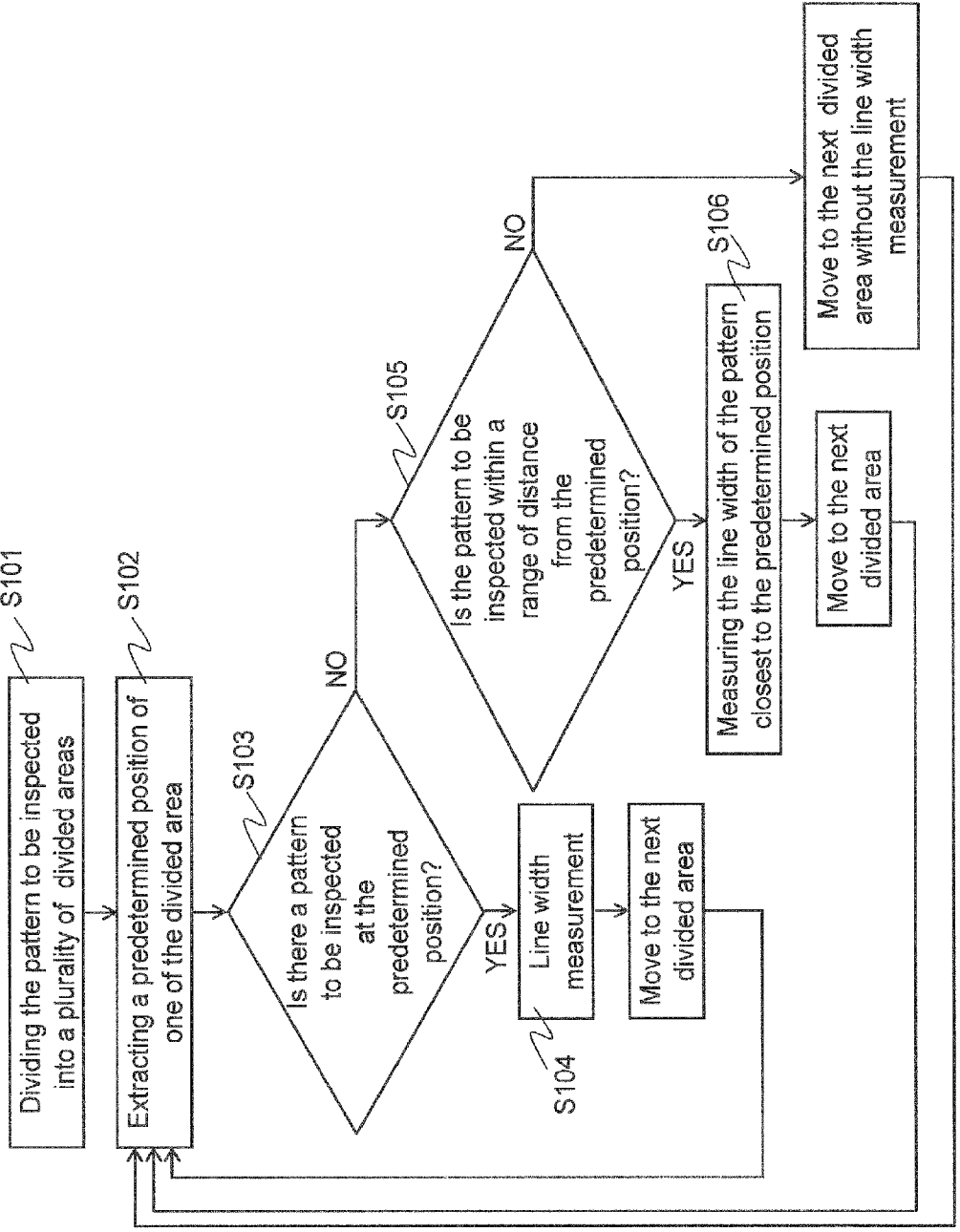
FIG. 13 is one example of a flowchart illustrating the method for measuring a line width in the step of obtaining a second line width error according to the second embodiment.

FIG. 13 is one example of a flowchart illustrating the method for measuring the line width in the second line width error obtaining step S17.

Firstly, an area of the pattern to be inspected is divided into a plurality of smaller areas (S101), hereinafter referred to as divided areas. For example, the area of the pattern to be inspected can be divided into 25 divided areas, that is, 5 areas in the X-direction and 5 areas in the Y-direction.

Next, a position corresponding to one of the divided areas (S101), is extracted (S102), and it is then determined whether there is a pattern to be inspected at the extracted position (S103). In the case where there is a pattern to be inspected at the extracted position, the line width of the pattern to be inspected is measured at the extracted position (S104). Then, after moving to the next area the same process is performed. The process is then repeated until line widths of all the divided areas have been measured.

In the case where the pattern to be inspected doesn't exist at the predetermined position in S103, it is then determined whether the pattern to be inspected exists within a distance r from the predetermined position (S105). In the case where the pattern to be inspected exists within the distance r from the predetermined position, the line width, of the pattern to be inspected, which is the closest to the predetermined position, is measured (S106). Then, after moving to the next area the same process is performed.

In the case where the pattern to be inspected doesn't exist within the distance r from the predetermined position in S105, the process of measuring a line width for this divided area is skipped, and the process continues in the next area, etc.

After the steps S104, S106, and S105 are respectively performed, after moving to the next divided area, the processes are then repeated starting from S102.

Each line width measured, as mentioned above, is compared with the line width corresponding to the reference image data to obtain the difference between measured line width and the line width corresponding to the reference image data. The obtained difference is the line width error (ΔCD) of the second line width error obtaining step S17.

<Line Width Error Correcting Step (S18)>

Referring to FIG. 11, in the line width error correcting step S18, the first line width error ΔCD1 obtained in the first line width error obtaining step S15 is corrected using the second line width error ΔCD2 obtained in the second line width error obtaining step S17. The line width error correcting step S18 can be performed by the line width error obtaining unit 122, shown in FIG. 1.

Firstly, line width error correcting data is generated using the measurement points of the second line width error ΔCD2. The measurement points of the second line width error ΔCD2 are less than the measurement points of the first line width error ΔCD1. Accordingly, the line width error correcting data is generated by interpolating the measurement points of the second line width error ΔCD2. Examples of the interpolation method include known methods such as, linear interpolation, interpolation in which a polynomial is used, and spline interpolation.

Next, the first line width error ΔCD1 is corrected with the above-mentioned line width error correcting data. Specifically, the first line width error ΔCD1 is corrected so that a difference between the first line width error ΔCD1 and data obtained from the line width error correcting data, is zero, thereby the correction value of the first line width error (ΔCD3) is obtained.

<ΔCD Map Generating Step (S19)>

The ΔCD Map generating step S19 is performed in the map generating unit 123 shown in FIG. 1. Specifically, the correction value of the first line width error (ΔCD3), and the measurement value of the position coordinate of the table 101 (transmitted from the position information unit 104) are transmitted from the line width error obtaining unit 122 to the map generating unit 123. In the map generating unit 123, a ΔCD map is generated by plotting the correction value of the first line width error (ΔCD3) at the corresponding position coordinate on the mask Ma.

As mentioned above, in the present embodiment, an optical image is obtained by illuminating light for transmission and illuminating light for reflection to the mask, at the same time, in the state where the polarized beam splitter is disposed. Then, an inspection for detecting a defect and a measurement of a line width are performed using the optical image, and as a result, the time required for obtaining the optical image can be shorter than the case where an optical image for the inspection for detecting a defect and an optical image for the measurement of the line width are obtained separately. Further, the line width error obtained from the optical image is corrected using the optical image data obtained by removing the polarized beam splitter from the light path of the light transmitted through the mask, as a result, an accurate line width can be obtained. Accordingly, an accurate ΔCD map can be obtained from this line width error. In the present embodiment, the inspection apparatus 100 generates the ΔCD map, however, the ΔCD map may be generated by an external unit of the inspection apparatus 100 using the line width error obtained by the inspection apparatus 100. The optical image for the correction can be obtained by dividing the pattern area to be inspected into a plurality of divided areas, and obtaining optical images of every divided area at a predetermined position within a distance r from the predetermined position. As a result, the optical image for the correction can be obtained in a shorter time than the optical image for the inspection for detecting a defect. Therefore, according to the present embodiment, an inspection for detecting a defect can be easily and accurately performed, and further, an accurate line width error, and an accurate ΔCD map can be obtained.

As mentioned above, the inspection apparatus and the inspection method according to the present invention are mentioned in each embodiment. However, the present invention is not limited to the inspection method, the inspection apparatus, and the inspection system mentioned in those embodiments. Various modifications to the present invention, improvements regarding possible combinations, and the like, may be performed. The scope of the present invention encompasses all inspection methods, inspection apparatuses, and inspection systems employing the elements of the present invention and variations thereof, which can be designed by those skilled in the art.

For example, in the above-mentioned embodiments, the polarized beam splitter is used for the purpose for dividing the light emitted from the light source to one light path for illuminating the inspection object with the light to be transmitted, and another light path for illuminating the inspection object by light to be reflected. However, the present embodiment is not limited to the polarized beam splitter, that is, any device which can divide the light beam can be used. For example, a beam splitter without the function of dividing the polarized light component can be used. Further, in the above-mentioned embodiments, the light emitted from one light source is divided to one light path for illuminating the inspection object with the light to be transmitted, and another light path for illuminating the inspection target with the light to be reflected, however in the present invention, the inspection apparatus can include one light source for illuminating the inspection object by light to be transmitted and a separate light source for illuminating the inspection target with the light to be reflected independently.

Further, the inspection apparatus illustrated in the embodiments described above includes the necessary components to achieve the desired outcome. However, the inspection apparatus and inspection system of the present invention can also include other well-known components necessary for line width error acquisition, attainment, and inspection. Each "unit" in the present invention, for example, the position measuring unit, the illuminating optical unit, the transmissive illuminating optical unit, the reflective illuminating optical unit, the comparing unit, the line width error obtaining unit, the laser length measuring unit, imaging optical unit, table control unit, position information unit, obtaining unit, optical image obtaining unit, map generating unit, reference image generating unit, master control unit, PBS moving control unit, etc., includes processing circuitry. This processing circuitry may include an electric circuit, a computer, a processor, a circuitry substrate, quantum circuitry, or a semiconductor device, etc. Further, processing circuitry common to all units, that is, identical circuitry, may be used, or individual processing circuitry specific to each unit may also be used. In the present invention a "unit" may also refer to a program operating on a computer. Alternatively, the "unit" may be constructed by, not only a software program, but also a combination of software, hardware, or firmware. In the case that the "unit" may be constructed by a program, the program can be recorded in a storage unit such as a magnetic disk device.

Further features of the present invention may be summarized as follows.

According to another aspect of the present invention, an inspection apparatus, comprising a map generating unit configured to generate a map of relationships between line width errors and position coordinates on the inspection object using the position coordinates of the table.

According to another aspect of the present invention, an inspection apparatus, comprising a beam splitter configured to be shared between a transmissive illuminating optical unit and a reflective illuminating optical unit, wherein the light emitted from the light source is divided to one light path for transmitting through the beam splitter, illuminating the inspection object, and transmitting through the inspection object, and another light path for reflecting by the beam splitter, illuminating the inspection object, and reflecting by the inspection object.

According to another aspect of the present invention, an inspection apparatus, wherein the beam splitter is a polarized beam splitter.

According to another aspect of the present invention, an inspection apparatus, comprising a first quarter-wavelength plate configured to change linearly polarized light to circularly polarized light, wherein the first quarter-wavelength plate is disposed in the transmissive illuminating optical unit, and a second quarter-wavelength plate is configured to change circularly polarized light transmitted through the inspection object to linearly polarized light, wherein the light source emits linearly polarized light, and wherein the light reflected by the polarized beam splitter is changed to the circularly polarized light by the second quarter-wavelength plate, reflected by the inspection object, and transmitted through the second quarter-wavelength plate to change the circularly polarized light to linearly polarized light of which the polarized direction is rotated by 90 degrees.

According to another aspect of the present invention, an inspection apparatus, comprising a reference image data generating unit configured to generate the reference image data.

According to another aspect of the present invention, an inspection method, wherein in a first optical image data obtaining step, optical image data is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, transmitting the linearly polarized light through the polarized beam splitter, causing the light transmitted through the polarized beam splitter to be incident to the first sensor, wherein the first sensor converts the optical image of the inspection object to an electric signal, and by changing linearly polarized light emitted from the light source to circularly polarized light by the second quarter-wavelength plate, illuminating the inspection object by the circularly polarized light, changing the circularly polarized light reflected by the inspection object to linearly polarized light by the second quarter-wavelength plate, transmitting the linearly polarized light through the polarized beam splitter, causing the light transmitted through the polarized beam splitter to be incident to the second sensor, wherein the second sensor converts the optical image of the inspection object to an electric signal, and wherein in the second optical image data obtaining step, optical image data is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, causing the linearly polarized light to be incident to the first sensor without transmission through the polarized beam splitter, wherein the first sensor converts the optical image of the inspection object to an electric signal.

According to another aspect of the present invention, an inspection method, wherein the light emitted from the light source is divided by a beam splitter, the transmissive illumination to the inspection object is performed by changing the linearly polarized light transmitted through the beam splitter to circularly polarized light by the first quarter-wavelength plate, and illuminating the circularly polarized light to the inspection object, and the reflective illumination to the inspection object is performed by changing the linearly polarized light reflected by the beam splitter to circularly polarized light by the second quarter-wavelength plate, and illuminating the circularly polarized light to the inspection object.

According to another aspect of the present invention, an inspection method, wherein the beam splitter is a polarized beam splitter.

According to another aspect of the present invention, an inspection method, wherein in the reference image data generating step, reference image data is generated from design data of the pattern, and wherein in the defect detecting step, a defect of the pattern is detected by comparing the reference image data with the optical image data obtained in the first optical image data obtaining step.

According to another aspect of the present invention, an inspection method, wherein in the reference image data generating step, reference image data is generated from design data of the pattern, and wherein in the line width error obtaining step, a difference between a line width of the pattern of the reference image data, and a line width of the pattern of the optical image data obtained in the second optical image data obtaining step, is obtained.

According to another aspect of the present invention, an inspection method wherein, in a line width error map generating step a map of relationships between line width errors and position coordinates on the inspection object is generated.

According to another aspect of the present invention, an inspection method, wherein in the first optical image data obtaining step, optical image data is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, transmitting the linearly polarized light through the polarized beam splitter, causing the light transmitted through the polarized beam splitter to be incident to the first sensor, wherein the first sensor converts the optical image of the inspection object to an electric signal, and by changing linearly polarized light emitted from the light source to circularly polarized light by the second quarter-wavelength plate, illuminating the inspection object by the circularly polarized light, changing the circularly polarized light reflected by the inspection object to linearly polarized light by the second quarter-wavelength plate, transmitting the linearly polarized light through the polarized beam splitter, causing the light transmitted through the polarized beam splitter to be incident to the second sensor, wherein the second sensor converts the optical image of the inspection object to an electric signal, and in the second optical image data obtaining step, optical image data of a predetermined area of the inspection object is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, causing the linearly polarized light to be incident to the first sensor without transmission through the polarized beam splitter, wherein the first sensor converts the optical image of the inspection object to an electric signal.

According to another aspect of the present invention, an inspection method, wherein the light emitted from the light source is divided by a beam splitter, the transmissive illumination to the inspection object is performed by changing the linearly polarized light transmitted through the beam splitter to circularly polarized light by the first quarter-wavelength plate, and illuminating the circularly polarized light to the inspection object, and the reflective illumination to the inspection object is performed by changing the linearly polarized light reflected by the beam splitter to circularly polarized light by the second quarter-wavelength plate, and illuminating the circularly polarized light to the inspection object.

According to another aspect of the present invention, an inspection method, wherein the beam splitter is a polarized beam splitter.

According to another aspect of the present invention, an inspection method, wherein in a reference image data generating step, reference image data is generated from design data of the pattern, and wherein in the defect detecting step, a defect of the pattern is detected by comparing the reference image data with the optical image data obtained in the first optical image data obtaining step.

According to another aspect of the present invention, an inspection method, wherein in a reference image data generating step, reference image data is generated from design data of the pattern of the inspection object, and wherein in the first line width error obtaining step, a difference between a line width of the pattern of the reference image data, and a line width of the pattern of the optical image data obtained in the first optical image data obtaining step, is obtained, and wherein in the second line width error obtaining step, a difference between a line width of the pattern of the reference image data, and a line width of the pattern of the optical image data obtained in the second optical image data obtaining step, is obtained.

According to another aspect of the present invention, an inspection method, wherein in a line width error map generating step a map of relationships between line width errors is generated, corrected in the line width error correcting step, and position coordinates on the inspection object.

What is claimed is:
1. An inspection apparatus comprising:
a table configured to support an inspection object;
a position measuring unit configured to measure a position coordinate of the table;
a light source configured to emit light for illuminating the inspection object;
an illuminating optical unit, wherein the illuminating optical unit includes:
a transmissive illuminating optical unit configured to illuminate the inspection object with the light emitted from the light source, wherein the light is transmitted through the inspection object;
a reflective illuminating optical unit configured to illuminate the inspection object with the light emitted from the light source, wherein the light is reflected by the inspection object;
a first sensor, wherein the light transmitted through the inspection object by the transmissive illuminating optical unit, is incident thereto, configured to convert an optical image of the inspection object to an electric signal;
a second sensor, wherein the light reflected by the inspection object by the reflective illuminating optical unit, is incident thereto, configured to convert an optical image of the inspection object to an electric signal;
a comparing unit configured to detect a defect of a pattern of the inspection object by comparing optical image data output from at least one of the first sensor and the second sensor with reference image data generated from design data of the pattern, corresponding to the optical image data;
a line width error obtaining unit configured to obtain a line width error by comparing a line width obtained from design data of the pattern and a line width of the pattern obtained from the optical image data; and
a polarized beam splitter configured to be movable between the inspection object and the first sensor, and between the inspection object and the second sensor, wherein in the case where the polarized beam splitter is disposed along the light path of the light for illuminating the inspection object with the light to be transmitted, the polarized beam splitter is also disposed along the light path for illuminating the inspection object with the light to be reflected.

2. The inspection apparatus according to claim 1, further comprising:
a map generating unit configured to generate a map of relationships between line width errors and position coordinates on the inspection object using the position coordinates of the table.

3. The inspection apparatus according to claim 1, further comprising:
a beam splitter configured to be shared between the transmissive illuminating optical unit and the reflective illuminating optical unit,
wherein the light emitted from the light source is divided to one light path for transmitting through the beam splitter, illuminating the inspection object, and transmitting through the inspection object, and another light path for reflecting by the beam splitter, illuminating the inspection object, and reflecting by the inspection object.

4. The inspection apparatus according to claim 3, wherein the beam splitter is a polarized beam splitter.

5. The inspection apparatus according to claim 1, further comprising:
a first quarter-wavelength plate configured to change linearly polarized light to circularly polarized light, wherein the first quarter-wavelength plate is disposed in the transmissive illuminating optical unit; and
a second quarter-wavelength plate configured to change circularly polarized light transmitted through the inspection object to linearly polarized light;
wherein the light source emits linearly polarized light,
wherein the light reflected by the polarized beam splitter is changed to the circularly polarized light by the second quarter-wavelength plate, reflected by the inspection object, and transmitted through the second quarter-wavelength plate to change the circularly polarized light to linearly polarized light of which the polarized direction is rotated by 90 degrees.

6. The inspection apparatus according to claim 1, further comprising:
a reference image data generating unit configured to generate the reference image data.

7. An inspection method comprising:
a first optical image data obtaining step of obtaining optical image data by illuminating an inspection object by light emitted from a light source, transmitting the light transmitted through the inspection object, through a polarized beam splitter, causing the light transmitted through the polarized beam splitter to be incident to a first sensor, wherein the first sensor converts an optical image of the inspection object to an electric signal, and
obtaining optical image data by illuminating the inspection object by light emitted from the light source, transmitting the light reflected by the inspection object, through the polarized beam splitter, causing the light transmitted through the polarized beam splitter to be incident to a second sensor, wherein the second sensor converts the optical image of the inspection object to an electric signal;
a defect detecting step of detecting a defect of a pattern of the inspection object using the optical image data obtained in the first optical image data obtaining step;
a second optical image data obtaining step of obtaining optical image data by illuminating the inspection object by light emitted from the light source, causing the light transmitted through the inspection object to be incident to the first sensor without transmission through the polarized beam splitter, wherein the first sensor converts the optical image of the inspection object to an electric signal; and
a line width error obtaining step of obtaining a difference between a line width obtained from design data of the pattern, and a line width of the pattern of the optical image data obtained in the second optical image data obtaining step.

8. The inspection method according to claim 7,
wherein in the first optical image data obtaining step, optical image data is obtained by changing linearly polarized light emitted from the light source to circularly polarized light by a first quarter-wavelength plate, illuminating the inspection object by the circularly polarized light, changing the circularly polarized light transmitted through the inspection object to linearly polarized light by a second quarter-wavelength plate, transmitting the linearly polarized light through the polarized beam splitter, causing the light transmitted through the polarized beam splitter to be incident to the first sensor, wherein the first sensor converts the optical image of the inspection object to an electric signal, and
by changing linearly polarized light emitted from the light source to circularly polarized light by the second quarter-wavelength plate, illuminating the inspection object by the circularly polarized light, changing the circularly polarized light reflected by the inspection object to linearly polarized light by the second quarter-wavelength plate, transmitting the linearly polarized light through the polarized beam splitter, causing the light transmitted through the polarized beam splitter to be incident to the second sensor, wherein the second sensor converts the optical image of the inspection object to an electric signal; and
in the second optical image data obtaining step, optical image data is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, causing the linearly polarized light to be incident to the first sensor without transmission through the polarized beam splitter, wherein the first sensor converts the optical image of the inspection object to an electric signal.

9. The inspection method according to claim 8,
wherein the light emitted from the light source is divided by a beam splitter,
transmissive illumination to the inspection object is performed by changing the linearly polarized light transmitted through the beam splitter to circularly polarized light by the first quarter-wavelength plate, and illuminating the circularly polarized light to the inspection object; and
reflective illumination to the inspection object is performed by changing the linearly polarized light reflected by the beam splitter to circularly polarized light by the second quarter-wavelength plate, and illuminating the circularly polarized light to the inspection object.

10. The inspection method according to claim 9, wherein the beam splitter is a polarized beam splitter.

11. The inspection method according to claim 7, further comprising:
a reference image data generating step of generating reference image data from design data of the pattern,
wherein in the defect detecting step, a defect of the pattern is detected by comparing the reference image data with the optical image data obtained in the first optical image data obtaining step.

12. The inspection method according to claim 7, further comprising:
a reference image data generating step of generating reference image data from design data of the pattern,
wherein in the line width error obtaining step, a difference between a line width of the pattern of the reference image data, and a line width of the pattern of the optical image data obtained in the second optical image data obtaining step, is obtained.

13. The inspection method according to claim 7, further comprising:
a line width error map generating step of generating a map of relationships between line width errors and position coordinates on the inspection object.

14. An inspection method comprising:
a first optical image data obtaining step of obtaining optical image data by illuminating an inspection object by light emitted from a light source, transmitting the light transmitted through the inspection object through a polarized beam splitter, causing the light transmitted through the inspection object to be incident to a first sensor, wherein the first sensor converts the optical image of the inspection object to an electric signal, and obtaining optical image data by illuminating the inspection object by light emitted from the light source, transmitting the light reflected by the inspection object through the polarized beam splitter, causing the light transmitted through the polarized beam splitter to be incident to a second sensor, wherein the second sensor converts the optical image of the inspection object to an electric signal;
a defect detecting step of detecting a defect of a pattern of the inspection object using the optical image data obtained in the first optical image data obtaining step;
a first line width error obtaining step of obtaining a difference between a line width obtained from design data of the pattern, and a line width of the pattern of the optical image data obtained in the first optical image data obtaining step;
a second optical image data obtaining step of obtaining optical image data of a predetermined area of the inspection object by illuminating the inspection object by light emitted from a light source, causing the light transmitted through the inspection object to be incident to the first sensor without transmission through the polarized beam splitter, wherein the first sensor converts the optical image of the inspection object to an electric signal;
a second line width error obtaining step of obtaining a difference between a line width obtained from design data of the pattern, and a line width of the pattern of the optical image data obtained in the second optical image data obtaining step; and
a line width error correcting step of correcting a line width error obtained in the first line width error obtaining step, using the line width error obtained in the second line width error obtaining step.

15. The inspection method according to claim 14,
wherein in the first optical image data obtaining step, optical image data is obtained by changing linearly polarized light emitted from the light source to circularly polarized light by a first quarter-wavelength plate, illuminating the inspection object by the circularly polarized light, changing the circularly polarized light transmitted through the inspection object to linearly polarized light by a second quarter-wavelength plate, transmitting the linearly polarized light through the polarized beam splitter, causing the light transmitted through the polarized beam splitter to be incident to the first sensor, wherein the first sensor converts the optical image of the inspection object to an electric signal, and
by changing linearly polarized light emitted from the light source to circularly polarized light by the second quarter-wavelength plate, illuminating the inspection object by the circularly polarized light, changing the circularly polarized light reflected by the inspection object to linearly polarized light by the second quarter-wavelength plate, transmitting the linearly polarized light through the polarized beam splitter, causing the light transmitted through the polarized beam splitter to be incident to the second sensor, wherein the second sensor converts the optical image of the inspection object to an electric signal; and
in the second optical image data obtaining step, optical image data of a predetermined area of the inspection object is obtained by changing linearly polarized light emitted from the light source to circularly polarized light by the first quarter-wavelength plate, illuminating the inspection object by the circularly polarized light, changing the circularly polarized light transmitted through the inspection object to linearly polarized light by the second quarter-wavelength plate, causing the linearly polarized light to be incident to the first sensor without transmission through the polarized beam splitter, wherein the first sensor converts the optical image of the inspection object to an electric signal.

16. The inspection method according to claim 15,
wherein the light emitted from the light source is divided by a beam splitter,
transmissive illumination to the inspection object is performed by changing the linearly polarized light transmitted through the beam splitter to circularly polarized light by the first quarter-wavelength plate, and illuminating the circularly polarized light to the inspection object; and
reflective illumination to the inspection object is performed by changing the linearly polarized light reflected by the beam splitter to circularly polarized light by the second quarter-wavelength plate, and illuminating the circularly polarized light to the inspection object.

17. The inspection method according to claim 16, wherein the beam splitter is a polarized beam splitter.

18. The inspection method according to claim 14, further comprising:
a reference image data generating step of generating reference image data from design data of the pattern,
wherein in the defect detecting step, a defect of the pattern is detected by comparing the reference image data with the optical image data obtained in the first optical image data obtaining step.

19. The inspection method according to claim 14, further comprising:
a reference image data generating step of generating reference image data from design data of the pattern of the inspection object,
wherein in the first line width error obtaining step, a difference between a line width of the pattern of the reference image data, and a line width of the pattern of the optical image data obtained in the first optical image data obtaining step, is obtained; and
wherein in the second line width error obtaining step, a difference between a line width of the pattern of the reference image data, and a line width of the pattern of the optical image data obtained in the second optical image data obtaining step, is obtained.

20. The inspection method according to claim 14, further comprising:
a line width error map generating step of generating a map of relationships between line width errors, corrected in the line width error correcting step, and position coordinates on the inspection object.

* * * * *